United States Patent [19]

Miyasaka et al.

[11] Patent Number: 5,112,835
[45] Date of Patent: May 12, 1992

[54] 6-SUBSTITUTED ACYCLOPYRIMIDINE NUCLEOSIDE DERIVATIVES AND ANTIVIRAL AGENTS CONTAINING THE SAME AS ACTIVE INGREDIENT THEREOF

[75] Inventors: Tadashi Miyasaka; Hiromichi Tanaka, both of Yokohama, Japan; Erik D. A. De Clercq, Leuven, Belgium; Masanori Baba, Fukushima, Japan; Richard T. Walker, Birmingham, United Kingdom; Masaru Ubasawa, Yokohama, Japan

[73] Assignee: Mitsubishi Kasei Corporation, Tokyo, Japan

[21] Appl. No.: 449,930

[22] PCT Filed: Mar. 31, 1989

[86] PCT No.: PCT/JP89/00347
  § 371 Date: Nov. 21, 1989
  § 102(e) Date: Nov. 21, 1989

[87] PCT Pub. No.: WO89/09213
  PCT Pub. Date: Oct. 5, 1989

[30] Foreign Application Priority Data

Mar. 31, 1988 [JP] Japan .................................. 63-76677

[51] Int. Cl.$^5$ .................. C07D 239/46; C07D 239/47; C07D 239/54; C07D 239/60
[52] U.S. Cl. ..................................... 544/302; 544/301; 544/303; 544/304; 544/305; 544/306; 544/309; 544/310; 544/313; 544/314; 544/317
[58] Field of Search ............... 544/309, 313, 314, 317, 544/302, 303, 301, 304, 305, 306; 514/269

[56] References Cited

U.S. PATENT DOCUMENTS 3,947,444  3/1976  Giller et al. ........................ 544/312
4,347,360  8/1982  Ogilvie ................................ 544/276
4,415,573  11/1983  Ochi et al. .......................... 544/312

FOREIGN PATENT DOCUMENTS 49-36685  4/1974  Japan .
50-32186  3/1975  Japan .
51-88974  8/1976  Japan .
57-738774  3/1982  Japan .

OTHER PUBLICATIONS

Drabikowska et al., CA107-129717w(1987).
Miyasaka et al., CA 112-77870x(1990).
Tanaka et al., CA 114-43451n(1991).

Primary Examiner—Cecilia Shen
Attorney, Agent, or Firm—James H. Laughlin, Jr.

[57] ABSTRACT 6-substitutted acyclopyrimidine nucleoside derivatives represented by the following general formula I:

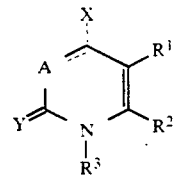

wherein $R^1$ represents a hydrogen or halogen atom or a group of alkyl, alkenyl, alkynyl, alkylcarbonyl, arylcarbonyl, arylcarbonylalkyl, arylthio or aralkyl; $R^2$ represents a group of arylthio, alkylthio, cycloalkylthio, aryl sulfoxide, alkyl sulfoxide, cycloalkyl sulfoxide, alkenyl, alkynyl, aralkyl, arylcarbonyl, arylcarbonylalkyl or aryloxy; $R^3$ represents a hydroxyalkyl group of which alkyl portion may contain an oxygen atom; X represents an oxygen or sulfur atom or amino group; Y represents an oxygen or sulfur atom; and A represents =N— or —NH— or pharmaceutically acceptable salts thereof, processes for their preparation and antiviral agents containing them as active ingredients.

18 Claims, No Drawings

6-SUBSTITUTED ACYCLOPYRIMIDINE NUCLEOSIDE DERIVATIVES AND ANTIVIRAL AGENTS CONTAINING THE SAME AS ACTIVE INGREDIENT THEREOF

TECHNICAL FIELD

The present invention relates to novel 6-substituted acyclopyrimidine derivatives, antiviral agents containing the derivatives as the active ingredients and a process for preparation of the derivatives.

BACKGROUND ART

Infectious diseases caused by human acquired immunodeficiency virus (HIV), which is a type of retrovirus, have recently become a serious social problem. A compound of 3'-deoxy-3'-azidothymidine is known as a nucleoside compound used in the clinical treatment of HIV-infection. However, this compound has side-effects since it also exhibits considerable toxicity in the host cell.

Although some 2',3'-dideoxyribonucleosides are known as nucleoside compounds exhibiting an anti-retroviral activity, it is still necessary to develop a substance possessing a higher activity and lower toxicity to the host cell (Hiroaki Mitsuya, Bodily Defense, Vol. 4, pp. 213 to 223 (1987)).

On the other hand, various acyclonucleoside compounds have been synthesized since Acyclovir (acycloguanosine) was developed as an antiviral substance effective against herpes virus (C. K. Chu and S. J. Culter, J. Heterocyclic Chem., 23, p. 289 (1986)). However, no acyclonucleoside compound having a sufficient activity especially against retroviruses has yet been discovered.

We have focussed our attention on 6-substituted acyclopyrimidine nucleoside compounds and have synthesized various novel 6-substituted acyclopyrimidine nucleoside derivatives and screened those compounds to detect an effective antiviral agent, especially to the retrovirus. Some 6-substituted acyclopyrimidine nucleoside compounds such as 6-fluoro substituted derivatives, 6-alkylamino substituted derivatives (DD-232492-A) and 6-methyl substituted derivatives (C.A. 107, 129717w (1987)), are known; however, the anti-retroviral activity of these compounds has not been described. As a result of our investigation, it was found that specific 6-substituted pyrimidine nucleoside compounds according to the invention satisfy the above demand which enables one to provide effective anti-retroviral agents.

SUMMARY OF THE INVENTION

The present invention concerns a 6-substituted acyclopyrimidine nucleoside derivative represented by the following general formula I:

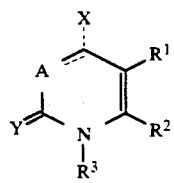

wherein $R^1$ represents a hydrogen or halogen atom or a group of alkyl, alkenyl, alkynyl, alkylcarbonyl, arylcarbonyl, arylcarbonylalkyl, arylthio or aralkyl; $R^2$ represents a group of arylthio, alkylthio, cycloalkylthio, aryl sulfoxide, alkyl sulfoxide, cycloalkyl sulfoxide, alkenyl, alkynyl, aralkyl, arylcarbonyl, arylcarbonylalkyl or aryloxy; $R^3$ represents a hydroxyalkyl group of which alkyl portion may contain an oxygen atom; X represents an oxygen or sulfur atom or an amino group; Y represents an oxygen or sulfur atom; and A represents =N— or —NH—, or a pharmaceutically acceptable salt thereof.

The present invention also concerns a process for the preparation of the 6-substituted acyclopyrimidine nucleoside derivative of formula I.

The present invention further concerns an antiviral agent containing as the active ingredient a 6-substituted acyclopyrimidine nucleoside derivative of formula I or a pharmaceutically acceptable salt thereof.

DETAILED DESCRIPTION OF THE INVENTION

The 6-substituted acyclopyrimidine derivative according to the invention is represented by the general formula I. In the general formula I, the groups of $R^1$, $R^2$ and $R^3$ may be optionally substituted with one or more suitable substituents.

The group of $R^1$ represents a hydrogen atom; a halogen atom such as a chlorine, iodine, bromine and fluorine atom; an alkyl group such as a methyl, ethyl, n-propyl, i-propyl and n-butyl group; an alkenyl group such as vinyl, propenyl, butenyl, phenylvinyl, bromovinyl, cyanovinyl, alkoxycarbonylvinyl and carbamoylvinyl group; an alkynyl group such as an ethynyl, propynyl and phenylethynyl group; an alkylcarbonyl group such as an acetyl, propionyl and i-butyryl group; an arylcarbonyl group such as benzoyl and naphthoyl group; an arylcarbonylalkyl group such as a phenacyl group; an arylthio group such as a phenylthio, tolylthio and naphthylthio group; or an aralkyl group such as a benzyl group.

The group of $R^2$ represents an arylthio group such as a phenylthio and naphthylthio group, which may be optionally substituted with one or more substituents selected from a halogen atom such as a chlorine, iodine, bromine and fluorine atom, alkyl group such as a methyl, ethyl, propyl, butyl and pentyl group, halogenated alkyl group such as a trifluoromethyl group, alkoxy group such as a methoxy, ethoxy, propoxy and butoxy group, hydroxy group, nitro group, amino group, cyano group and acyl group such as an acetyl group; an alkylthio group such as a methylthio, ethylthio, propylthio, butylthio and pentylthio group; a cycloalkylthio group such as a cyclopentylthio, cyclohexylthio and cycloheptylthio group, which may be optionally substituted with one or more of the substituents mentioned above as the substituent of the arylthio group; an aryl sulfoxide group such as a phenyl sulfoxide group; an alkyl sulfoxide group such as a methyl sulfoxide, ethyl sulfoxide and butyl sulfoxide group; a cycloalkyl sulfoxide group such as cyclopentyl sulfoxide, cyclohexyl sulfoxide group; an alkenyl group such as vinyl, propenyl and phenylvinyl group; an alkynyl group such as an ethynyl, propynyl and phenylethynyl group; an aralkyl group such as a benzyl group; an arylcarbonyl group such as a benzoyl group; an arylcarbonylalkyl group such as a phenacyl group; or a aryloxy group such as a phenyloxy group.

The group of $R^3$ represents a hydroxyalkyl group, preferably an ω-hydroxyalkoxy alkyl group such as (2-hydroxyethoxy)methyl, (3-hydroxypropoxy)methyl, (2,3-dihydroxypropoxy)methyl, 1-(2-hydroxyethoxy)ethyl, [2-hydroxy-1-(hydroxymethyl)ethoxy]methyl and (2-hydroxy-1-methylethoxy)methyl group.

The symbol of X represents an oxygen or sulfur atom or an amino group.

The symbol of Y represents an oxygen or sulfur atom.

The symbol of A represents =N— or —NH—.

The preferred compounds according to the invention have $R^1$ of a hydrogen atom, halogen atom, $C_1$ to $C_5$ alkyl group or $C_2$ to $C_5$ alkenyl group, particularly, $C_1$ to $C_5$ alkyl group; $R^2$ of $C_6$ to $C_{10}$ arylthio, $C_3$ to $C_{10}$ cycloalkylthio or $C_7$ to $C_{11}$ aralkyl group, particularly those substituted with one or more substituents selected from halogen atom, $C_1$ to $C_5$ alkyl group, $C_1$ to $C_5$ alkoxy group and nitro group; $R^3$ of hydroxyalkoxyalkyl group having 2 to 6 carbon atoms, particularly 2-hydroxyethoxymethyl group; X of oxygen or sulfur atom; and Y of oxygen or sulfur atom.

Examples of the preferred compound of the invention are listed in Table 1 below.

TABLE-1

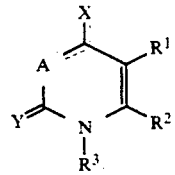

[I]

| Compound No. | $R^1$ | $R^2$ | $R^3$ | X | Y | A | Melting point (°C.) |
|---|---|---|---|---|---|---|---|
| 1 | —CH₃ | —S—C₆H₅ | HO−\O−\ | O | O | —NH— | 123–124 |
| 2 | —H | —S—C₆H₅ | HO−\O−\ | O | O | —NH— | 138–140 |
| 3 | —F | —S—C₆H₅ | HO−\O−\ | O | O | —NH— | 116–117 |
| 4 | —Cl | —S—C₆H₅ | HO−\O−\ | O | O | —NH— | 121–122 |
| 5 | —Br | —S—C₆H₅ | HO−\O−\ | O | O | —NH— | 80–82 |
| 6 | —CH₃ | —S—(2-CH₃-C₆H₄) | HO−\O−\ | O | O | —NH— | 138–139 |
| 7 | —CH₃ | —S—(3-CH₃-C₆H₄) | HO−\O−\ | O | O | —NH— | 104–105 |
| 8 | —CH₃ | —S—(4-CH₃-C₆H₄) | HO−\O−\ | O | O | —NH— | 127–128 |

TABLE-1-continued

| Compound No. | R¹ | R² | R³ | X | Y | A | Melting point (°C.) |
|---|---|---|---|---|---|---|---|
| 9 | —CH₃ | —S—(2-Cl-C₆H₄) | HO-oxolanyl | O | O | —NH— | 163-165 |
| 10 | —CH₃ | —S—(3-Cl-C₆H₄) | HO-oxolanyl | O | O | —NH— | 72 |
| 11 | —CH₃ | —S—(4-Cl-C₆H₄) | HO-oxolanyl | O | O | —NH— | 144-145 |
| 12 | —CH₃ | —S—(2-OCH₃-C₆H₄) | HO-oxolanyl | O | O | —NH— | 151-153 |
| 13 | —CH₃ | —S—(3-OCH₃-C₆H₄) | HO-oxolanyl | O | O | —NH— | 118-119 |
| 14 | —CH₃ | —S—(4-OCH₃-C₆H₄) | HO-oxolanyl | O | O | —NH— | 95-97 |
| 15 | —CH₃ | —S—(4-F-C₆H₄) | HO-oxolanyl | O | O | —NH— | 103 |
| 16 | —CH₃ | —S—(2-NO₂-C₆H₄) | HO-oxolanyl | O | O | —NH— | 185-187 |
| 17 | —CH₃ | —S—(3-NO₂-C₆H₄) | HO-oxolanyl | O | O | —NH— | 118-120 |
| 18 | —CH₃ | —S—(4-NO₂-C₆H₄) | HO-oxolanyl | O | O | —NH— | 201-203 |

TABLE-1-continued

[I]

| Compound No. | R¹ | R² | R³ | X | Y | A | Melting point (°C.) |
|---|---|---|---|---|---|---|---|
| 19 | —CH₃ | —S—C₆H₄—CN (4-cyanophenylthio) | HO-furanyl | O | O | —NH— | 218–219 |
| 20 | —CH₃ | —S—C₆H₄—COCH₃ (4-acetylphenylthio) | HO-furanyl | O | O | —NH— | 107–108 |
| 21 | —CH₃ | —S—C₆H₄—CH₂CH₃ (2-ethylphenylthio) | HO-furanyl | O | O | —NH— | |
| 22 | —CH₃ | —S—CH₃ | HO-furanyl | O | O | —NH— | 138–141 |
| 23 | —CH₃ | —S—CH₂CH₃ | HO-furanyl | O | O | —NH— | 108–109 |
| 24 | —CH₃ | —S—(CH₂)₃—CH₃ | HO-furanyl | O | O | —NH— | 98–99 |
| 25 | —CH₃ | —S—cyclohexyl | HO-furanyl | O | O | —NH— | 123–124 |
| 26 | —CH₃ | —S—C₆H₄—CF₃ | HO-furanyl | O | O | —NH— | |
| 27 | —CH₃ | —S—C₆H₃—Cl₂ (2,4-dichlorophenylthio) | HO-furanyl | O | O | —NH— | |
| 28 | —CH₃ | —S—C₆H₃—(CH₃)₂ (2,4-dimethylphenylthio) | HO-furanyl | O | O | —NH— | |
| 29 | —CH₃ | —S—naphthyl—OH (6-hydroxy-2-naphthylthio) | HO-furanyl | O | O | —NH— | 188 |

TABLE-1-continued

[I]

*Structure: pyrimidine-type ring with substituents X, R¹, R², A, Y, and N-R³*

| Compound No. | R¹ | R² | R³ | X | Y | A | Melting point (°C.) |
|---|---|---|---|---|---|---|---|
| 30 | —CH₃ | —S—C₆H₄ (phenylthio) | HO-CH₂-(oxiranyl) | O | O | —NH— | 92–93 |
| 31 | —CH₃ | —S—C₆H₄ | HO-CH(CH₃)-(oxiranyl) | O | O | —NH— | 138–140 |
| 32 | —CH₃ | —S—C₆H₄ | HO-CH₂-CH(O-)-CH₂-OH | O | O | —NH— | 161–162 |
| 33 | —CH₃ | —S—C₆H₄ | (HO)(HO)CH-(oxiranyl) | O | O | —NH— | 83–84 |
| 34 | —H | —S—C₆H₄ | HO-CH₂-(oxiranyl) | O | O | —NH— | 131–133 |
| 35 | —CH₃ | —S—C₆H₄(o-NH₂) | HO-CH₂-(oxiranyl) | O | O | —NH— | 140 |
| 36 | —CH₃ | —S—C₆H₄(m-NH₂) | HO-CH₂-(oxiranyl) | O | O | —NH— | 235–238 |
| 37 | —CH₃ | —S(=O)—C₆H₅ | HO-CH₂-(oxiranyl) | O | O | —NH— | 130 |
| 38 | —CH₃ | —C≡C—C₆H₅ | HO-CH₂-(oxiranyl) | O | O | —NH— | 214 |
| 39 | —CH₃ | —C≡C—CH₃ | HO-CH₂-(oxiranyl) | O | O | —NH— | 169 |
| 40 | —CH₃ | —C≡CH | HO-CH₂-(oxiranyl) | O | O | —NH— | 154 |

TABLE-1-continued

[I]

| Compound No. | R¹ | R² | R³ | X | Y | A | Melting point (°C.) |
|---|---|---|---|---|---|---|---|
| 41 | —CH₃ | —CH=CH—C₆H₅ | HO-furfuryl | O | O | —NH— | 144 |
| 42 | —CH₃ | —CH=CH—CH₃ | HO-furfuryl | O | O | —NH— | 97 |
| 43 | —CH₃ | —CH=CH₂ | HO-furfuryl | O | O | —NH— | 114 |
| 44 | —I | —S—C₆H₅ | HO-furfuryl | O | O | —NH— | 180–182 |
| 45 | —C≡C—C₆H₅ | —S—C₆H₅ | HO-furfuryl | O | O | —NH— | 146–148 |
| 46 | —C≡C—CH₃ | —S—C₆H₅ | HO-furfuryl | O | O | —NH— | 165–165.5 |
| 47 | —C≡CH | —S—C₆H₅ | HO-furfuryl | O | O | —NH— | 163–165 |
| 48 | —CH=CH—C₆H₅ | —S—C₆H₅ | HO-furfuryl | O | O | —NH— | 141–145 |
| 49 | —CH=CH—CH₃ | —S—C₆H₅ | HO-furfuryl | O | O | —NH— | |
| 50 | —CH=CH₂ | —S—C₆H₅ | HO-furfuryl | O | O | —NH— | 100–103 |
| 51 | —CH₂—C₆H₅ | —S—C₆H₅ | HO-furfuryl | O | O | —NH— | |
| 52 | —S—C₆H₅ | —S—C₆H₅ | HO-furfuryl | O | O | —NH— | 146–148 |

TABLE-1-continued

[I]

| Compound No. | R¹ | R² | R³ | X | Y | A | Melting point (°C.) |
|---|---|---|---|---|---|---|---|
| 53 | -C(=O)-C₆H₅ | -S-C₆H₅ | HO-tetrahydrofuranylmethyl | O | O | -NH- | 150-151 |
| 54 | -C(=O)-CH(CH₃)₂ | -S-C₆H₅ | HO-tetrahydrofuranylmethyl | O | O | -NH- | 144-145 |
| 55 | -CH₂-C(=O)-C₆H₅ | -S-C₆H₅ | HO-tetrahydrofuranylmethyl | O | O | -NH- | 151.5-153.5 |
| 56 | -H | -S-C₆H₅ | HO-tetrahydrofuranylmethyl | -NH₂ | O | -N= | 202 |
| 57 | -CH₃ | -S-C₆H₅ | HO-tetrahydrofuranylmethyl | -NH₂ | O | -N= | 220 |
| 58 | -H | -S-C₆H₅ | HO-tetrahydrofuranylmethyl | O | S | -NH- | 146 |
| 59 | -CH₃ | -S-C₆H₅ | HO-tetrahydrofuranylmethyl | O | S | -NH- | 107 |
| 60 | -H | -S-C₆H₅ | HO-tetrahydrofuranylmethyl | S | O | -NH- | 156 |
| 61 | -CH₃ | -S-C₆H₅ | HO-tetrahydrofuranylmethyl | S | O | -NH- | 114 |
| 62 | -CH₃ | -C(=O)-C₆H₅ | HO-tetrahydrofuranylmethyl | S | O | -NH- | |
| 63 | -CH₃ | -CH₂-C₆H₅ | HO-tetrahydrofuranylmethyl | S | O | -NH- | |

TABLE-1-continued $$[I]$$

(structure shown: pyrimidine-type ring with X at top, R¹, R², A, Y, and N-R³ substituents)

| Compound No. | R¹ | R² | R³ | X | Y | A |
|---|---|---|---|---|---|---|
| 64 | -CH=C(CH₃)₂ | -S-C₆H₅ | HO-(tetrahydrofuranyl-O-CH₂) | O | O | -NH- |
| 65 | -CH=C(C₆H₅)₂ | -S-C₆H₅ | HO-(tetrahydrofuranyl-O-CH₂) | O | O | -NH- |
| 66 | -CH=CH-COOC₂H₅ | -S-C₆H₅ | HO-(tetrahydrofuranyl-O-CH₂) | O | O | -NH- |
| 67 | -CH=CHC(O)NH₂ | -S-C₆H₅ | HO-(tetrahydrofuranyl-O-CH₂) | O | O | -NH- |
| 68 | -CH=CHBr | -S-C₆H₅ | HO-(tetrahydrofuranyl-O-CH₂) | O | O | -NH- |
| 69 | -CH=CHCN | -S-C₆H₅ | HO-(tetrahydrofuranyl-O-CH₂) | O | O | -NH- |
| 70 | -CH₂CH₃ | -S-C₆H₅ | HO-(tetrahydrofuranyl-O-CH₂) | O | O | -NH- |
| 71 | -CH₂CH₂CH₃ | -S-C₆H₅ | HO-(tetrahydrofuranyl-O-CH₂) | O | O | -NH- |
| 72 | -CH(CH₃)₂ | -S-C₆H₅ | HO-(tetrahydrofuranyl-O-CH₂) | O | O | -NH- |
| 73 | -CH₂CH₂CH₂CH₃ | -S-C₆H₅ | HO-(tetrahydrofuranyl-O-CH₂) | O | O | -NH- |

TABLE-1-continued

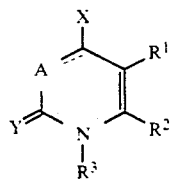
[I]

| Compound No. | R¹ | R² | R³ | X | Y | A | Melting point (°C.) |
|---|---|---|---|---|---|---|---|
| 74 | —CH₂—CH=CH₂ | —S—C₆H₅ | HO—CH₂—CH(OH)—CH₂—O— | O | O | —NH— | |
| 75 | —CH₂CH₂—C₆H₅ | —S—C₆H₅ | HO—CH₂—CH(OH)—CH₂—O— | O | O | —NH— | |
| 76 | —CH₃ | —S—CH(—CH₃)₂ | HO—CH₂—CH(OH)—CH₂—O— | O | O | —NH— | |
| 77 | —CH₃ | —S—C(—CH₃)₃ | HO—CH₂—CH(OH)—CH₂—O— | O | O | —NH— | |
| 78 | —CH₃ | —S—CH₂—C(—CH₃)₃ | HO—CH₂—CH(OH)—CH₂—O— | O | O | —NH— | |
| 79 | —CH₃ | —S(=O)—CH₃ | HO—CH₂—CH(OH)—CH₂—O— | O | O | —NH— | |
| 80 | —CH₃ | —S(=O)—CH(CH₃)₂ | HO—CH₂—CH(OH)—CH₂—O— | O | O | —NH— | |
| 81 | —CH₃ | —S(=O)—C₆H₁₁ | HO—CH₂—CH(OH)—CH₂—O— | O | O | —NH— | |
| 82 | —CH₃ | —S—(2-naphthyl) | HO—CH₂—CH(OH)—CH₂—O— | O | O | —NH— | |
| 83 | —CH₃ | —S—(1-naphthyl) | HO—CH₂—CH(OH)—CH₂—O— | O | O | —NH— | |
| 84 | —CH₃ | —S—CH₂—C₆H₅ | HO—CH₂—CH(OH)—CH₂—O— | O | O | —NH— | |

TABLE-1-continued

[I]

(structure with X, R¹, A, Y, N-R³, R²)

| Compound No. | R¹ | R² | R³ | X | Y | A | Melting point (°C.) |
|---|---|---|---|---|---|---|---|
| 85 | —CH₃ | —S—(3-isopropylphenyl) | HO-CH₂-tetrahydrofuranyl | O | O | —NH— | |
| 86 | —CH₃ | —S—(3-halophenyl) | HO-CH₂-tetrahydrofuranyl | O | O | —NH— | |
| 87 | —CH₃ | —S—(3-ethoxyphenyl) | HO-CH₂-tetrahydrofuranyl | O | O | —NH— | |
| 88 | —CH₃ | —S—(3-isopropoxyphenyl via CH(CH₃)₂-CHO) | HO-CH₂-tetrahydrofuranyl | O | O | —NH— | |
| 89 | —CH₃ | —S—(3-haloalkoxyphenyl) | HO-CH₂-tetrahydrofuranyl | O | O | —NH— | |
| 90 | —CH₃ | —CH₂—CH=CH₂ | HO-CH₂-tetrahydrofuranyl | O | O | —NH— | |
| 91 | —CH₃ | —CH=C(phenyl)₂ | HO-CH₂-tetrahydrofuranyl | O | O | —NH— | |
| 92 | —CH₃ | —CH₂CH₂—phenyl | HO-CH₂-tetrahydrofuranyl | O | O | —NH— | |

TABLE-1-continued

[I]

$$\text{structure with X, R}^1, R^2, R^3, Y, A, N$$

| Compound No. | $R^1$ | $R^2$ | $R^3$ | X | Y | A | Melting point (°C.) |
|---|---|---|---|---|---|---|---|
| 93 | —CH$_3$ | —O—C$_6$H$_5$ | HO—N=C(O)— (tetrahydrofuran-2-yl-methyl) | O | O | —NH— | |
| 94 | —CH$_3$ | —O—(3-CH$_3$-C$_6$H$_4$) | HO—N=C(O)— | O | O | —NH— | |
| 95 | —CH$_3$ | —O—(3-OCH$_3$-C$_6$H$_4$) | HO—N=C(O)— | O | O | —NH— | |
| 96 | —CH$_3$ | —O—(3-C(O)CH$_3$-C$_6$H$_4$) | HO—N=C(O)— | O | O | —NH— | |
| 97 | —CH$_3$ | —O—(3-CF$_3$-C$_6$H$_4$) | HO—N=C(O)— | O | O | —NH— | |
| 98 | —CH$_3$ | —O—(3-Cl-C$_6$H$_4$) | HO—N=C(O)— | O | O | —NH— | |
| 99 | —CH$_3$ | —O—(3-Br-C$_6$H$_4$) | HO—N=C(O)— | O | O | —NH— | |
| 100 | —CH$_3$ | —O—(3-F-C$_6$H$_4$) | HO—N=C(O)— | O | O | —NH— | |
| 101 | —CH$_3$ | —O—(3-NO$_2$-C$_6$H$_4$) | HO—N=C(O)— | O | O | —NH— | |

TABLE-1-continued

[I]

Structure: based on the general formula shown with X, R¹, R², R³, Y, A substituents on the ring.

| Compound No. | R¹ | R² | R³ | X | Y | A | Melting point (°C.) |
|---|---|---|---|---|---|---|---|
| 102 | —CH₃ | —S—(cyclopentyl, H) | HO-oxiranylmethyl | O | O | —NH— | |
| 103 | —CH₃ | —S—(cycloheptyl, H) | HO-oxiranylmethyl | O | O | —NH— | |
| 104 | —CH₃ | —S—(cyclohexyl, H) with CH₃ | HO-oxiranylmethyl | O | O | —NH— | |
| 105 | —CH₃ | —S—(cyclohexyl, H) with two CH₃ | HO-oxiranylmethyl | O | O | —NH— | |
| 106 | —CH₃ | —S—(cyclohexyl, H) with Cl | HO-oxiranylmethyl | O | O | —NH— | |
| 107 | —CH₃ | —S—(cyclohexyl, H) with two Cl | HO-oxiranylmethyl | O | O | —NH— | |
| 108 | —CH₃ | —S—(cyclohexyl, H) with COCH₃ | HO-oxiranylmethyl | O | O | —NH— | |
| 109 | —CH₃ | —S—(cyclohexyl, H) with two COCH₃ | HO-oxiranylmethyl | O | O | —NH— | |
| 110 | —CH₃ | —S—(cyclohexyl, H) with CF₃ | HO-oxiranylmethyl | O | O | —NH— | |

TABLE-1-continued

[I]

Structure: pyrimidine-type ring with X at top, A connecting to ring, Y=, R¹, R², R³ substituents

| Compound No. | R¹ | R² | R³ | X | Y | A | Melting point (°C.) |
|---|---|---|---|---|---|---|---|
| 111 | —CH₃ | —S—(cyclohexyl-F) | HO-tetrahydrofuran | O | O | —NH— | |
| 112 | —CH₃ | —S—(cyclohexyl-OCH₃) | HO-tetrahydrofuran | O | O | —NH— | |
| 113 | —CH₃ | —S—(cyclohexyl-(OCH₃)₂) | HO-tetrahydrofuran | O | O | —NH— | |
| 114 | —C(=O)CH₃ | —S—phenyl | HO-tetrahydrofuran | O | O | —NH— | |
| 115 | —C(=O)CH₂—CH₃ | —S—phenyl | HO-tetrahydrofuran | O | O | —NH— | |
| 116 | —C(=O)-naphthyl | —S—phenyl | HO-tetrahydrofuran | O | O | —NH— | |
| 117 | —S—C₆H₄—CH₃ | —S—phenyl | HO-tetrahydrofuran | O | O | —NH— | |
| 118 | —CH₃ | —S—(4-methylnaphthyl) | HO-tetrahydrofuran | O | O | —NH— | |
| 119 | —CH₃ | —S—(4-chloronaphthyl) | HO-tetrahydrofuran | O | O | —NH— | |

TABLE-1-continued

[I]

Structure: A–Y=(Y)–N(R³)–C(R²)=C(R¹)–C(=X) (with A between ring positions)

| Compound No. | R¹ | R² | R³ | X | Y | A | Melting point (°C.) |
|---|---|---|---|---|---|---|---|
| 120 | —CH₃ | —S-(phenyl with CF₃) (naphthyl) | HO-CH₂-O-CH₂- (tetrahydropyran-2-yl methyl) | O | O | —NH— | |
| 121 | —CH=CH-(naphthyl) | —S-phenyl | HO-CH₂-O-CH₂- | O | O | —NH— | |
| 123 | —CH=CH(OCH₃) | —S-phenyl | HO-CH₂-O-CH₂- | O | O | —NH— | |
| 124 | —CH=CH(OC₂H₅) | —S-phenyl | HO-CH₂-O-CH₂- | O | O | —NH— | |
| 125 | —CH=CH(NH₂) | —S-phenyl | HO-CH₂-O-CH₂- | O | O | —NH— | |
| 126 | —CH=CH(NO₂) | —S-phenyl | HO-CH₂-O-CH₂- | O | O | —NH— | |
| 127 | —C≡C-(naphthyl) | —S-phenyl | HO-CH₂-O-CH₂- | O | O | —NH— | |
| 128 | —C≡CCl | —S-phenyl | HO-CH₂-O-CH₂- | O | O | —NH— | |
| 129 | —C≡C—C₂H₅ | —S-phenyl | HO-CH₂-O-CH₂- | O | O | —NH— | |
| 130 | —C≡C—OCH₃ | —S-phenyl | HO-CH₂-O-CH₂- | O | O | —NH— | |

TABLE-1-continued

[I]

| Compound No. | R¹ | R² | R³ | X | Y | A | Melting point (°C.) |
|---|---|---|---|---|---|---|---|
| 131 | −C≡C−NH₂ | −S−C₆H₅ | HO-furanyl | O | O | −NH− | |
| 132 | −C≡C−CONH₂ | −S−C₆H₅ | HO-furanyl | O | O | −NH− | |
| 133 | −C(=O)−(3-CH₃-C₆H₄) | −S−C₆H₅ | HO-furanyl | O | O | −NH− | |
| 134 | −C(=O)−(3-OCH₃-C₆H₄) | −S−C₆H₅ | HO-furanyl | O | O | −NH− | |
| 135 | −C(=O)−(3-Cl-C₆H₄) | −S−C₆H₅ | HO-furanyl | O | O | −NH− | |
| 136 | −C(=O)−(3-NH₂-C₆H₄) | −S−C₆H₅ | HO-furanyl | O | O | −NH− | |
| 137 | −C(=O)−(3-NO₂-C₆H₄) | −S−C₆H₅ | HO-furanyl | O | O | −NH− | |
| 138 | −C(=O)−(3-CN-C₆H₄) | −S−C₆H₅ | HO-furanyl | O | O | −NH− | |
| 139 | −C₂H₄−C(=O)−C₆H₅ | −S−C₆H₅ | HO-furanyl | O | O | −NH− | |

TABLE-1-continued

[I]

| Compound No. | R¹ | R² | R³ | X | Y | A | Melting point (°C.) |
|---|---|---|---|---|---|---|---|
| 140 | -CH₂C(=O)-(2-naphthyl) | -S-phenyl | HO-oxetanyl | O | O | -NH- | |
| 141 | -CH₂C(=O)-(3-methylphenyl) | -S-phenyl | HO-oxetanyl | O | O | -NH- | |
| 142 | -CH₂C(=O)-(3-methoxyphenyl) | -S-phenyl | HO-oxetanyl | O | O | -NH- | |
| 143 | -CH₂C(=O)-(3-chlorophenyl) | -S-phenyl | HO-oxetanyl | O | O | -NH- | |
| 144 | -CH₂C(=O)-(3-aminophenyl) | -S-phenyl | HO-oxetanyl | O | O | -NH- | |
| 145 | -S-(2-naphthyl) | -S-phenyl | HO-oxetanyl | O | O | -NH- | |
| 146 | -S-(3-methoxyphenyl) | -S-phenyl | HO-oxetanyl | O | O | -NH- | |
| 147 | -S-(3-chlorophenyl) | -S-phenyl | HO-oxetanyl | O | O | -NH- | |
| 148 | -CH₂-(2-naphthyl) | -S-phenyl | HO-oxetanyl | O | O | -NH- | |

TABLE-1-continued

[I]

Structure: pyrimidine-like ring with X, R¹, R², A, Y, N-R³ substituents

| Compound No. | R¹ | R² | R³ | X | Y | A | Melting point (°C.) |
|---|---|---|---|---|---|---|---|
| 149 | -CH₂-C₆H₄-CH₃ (3-methyl) | -S-C₆H₅ | HO-CH(CH₂O-) | O | O | -NH- | |
| 150 | -CH₂-C₆H₄-OCH₃ (3-methoxy) | -S-C₆H₅ | HO-CH(CH₂O-) | O | O | -NH- | |
| 151 | -CH₂-C₆H₄-Cl (3-chloro) | -S-C₆H₅ | HO-CH(CH₂O-) | O | O | -NH- | |
| 152 | -CH₂-C₆H₄-F (3-fluoro) | -S-C₆H₅ | HO-CH(CH₂O-) | O | O | -NH- | |
| 153 | -CH₃ | -S-(cyclohexyl-NH₂) | HO-CH(CH₂O-) | O | O | -NH- | |
| 154 | -CH₃ | -S-(cyclooctyl) | HO-CH(CH₂O-) | O | O | -NH- | |
| 155 | -CH₃ | -S(=O)-(2-naphthyl) | HO-CH(CH₂O-) | O | O | -NH- | |
| 156 | -CH₃ | -S(=O)-C₆H₄-CH₃ (3-methyl) | HO-CH(CH₂O-) | O | O | -NH- | |
| 157 | -CH₃ | -S(=O)-C₆H₄-OCH₃ (3-methoxy) | HO-CH(CH₂O-) | O | O | -NH- | |

TABLE-1-continued

[1]

| Compound No. | R¹ | R² | R³ | X | Y | A | Melting point (°C.) |
|---|---|---|---|---|---|---|---|
| 158 | —CH₃ | 3-chlorophenyl-S(=O)— | HO-tetrahydrofuranyl | O | O | —NH— | |
| 159 | —CH₃ | 3-aminophenyl-S(=O)— | HO-tetrahydrofuranyl | O | O | —NH— | |
| 160 | —CH₃ | 3-acetylphenyl-S(=O)— | HO-tetrahydrofuranyl | O | O | —NH— | |
| 161 | —CH₃ | cyclopentyl-S(=O)— | HO-tetrahydrofuranyl | O | O | —NH— | |
| 162 | —CH₃ | 3-methylcyclohexyl-S(=O)— | HO-tetrahydrofuranyl | O | O | —NH— | |
| 163 | —CH₃ | 3-methoxycyclohexyl-S(=O)— | HO-tetrahydrofuranyl | O | O | —NH— | |
| 164 | —CH₃ | 3-chlorocyclohexyl-S(=O)— | HO-tetrahydrofuranyl | O | O | —NH— | |
| 165 | —CH₃ | 3-aminocyclohexyl-S(=O)— | HO-tetrahydrofuranyl | O | O | —NH— | |
| 166 | —CH₃ | 3-acetylcyclohexyl-S(=O)— | HO-tetrahydrofuranyl | O | O | —NH— | |

TABLE-1-continued

[I]

(structure shown: A ring with X, R¹, R², Y, N-R³ substituents)

| Compound No. | R¹ | R² | R³ | X | Y | A | Melting point (°C.) |
|---|---|---|---|---|---|---|---|
| 167 | —CH₃ | —CH=CH—(2-naphthyl) | HO-[furanyl] | O | O | —NH— | |
| 168 | —CH₃ | —CH=CHCl | HO-[furanyl] | O | O | —NH— | |
| 169 | —CH₃ | —CH=CH(OCH₃) | HO-[furanyl] | O | O | —NH— | |
| 170 | —CH₃ | —CH=CH(COCH₃) | HO-[furanyl] | O | O | —NH— | |
| 171 | —CH₃ | —CH=CH(NH₂) | HO-[furanyl] | O | O | —NH— | |
| 172 | —CH₃ | —C≡C—(2-naphthyl) | HO-[furanyl] | O | O | —NH— | |
| 173 | —CH₃ | —C≡C—OCH₃ | HO-[furanyl] | O | O | —NH— | |
| 174 | —CH₃ | —C≡C(COCH₃) | HO-[furanyl] | O | O | —NH— | |
| 175 | —CH₃ | —C≡CCl | HO-[furanyl] | O | O | —NH— | |
| 176 | —CH₃ | —C≡C—NH₂ | HO-[furanyl] | O | O | —NH— | |
| 177 | —CH₃ | —CH₂—(2-naphthyl) | HO-[furanyl] | O | O | —NH— | |
| 178 | —CH₃ | —CH₂—(3-methylphenyl) | HO-[furanyl] | O | O | —NH— | |
| 179 | —CH₃ | —CH₂—(3-methoxyphenyl) | HO-[furanyl] | O | O | —NH— | |

TABLE-1-continued

[Structure [1] at top showing the general formula with X, R¹, A, Y, N, R², R³ substituents]

| Compound No. | R¹ | R² | R³ | X | Y | A | Melting point (°C) |
|---|---|---|---|---|---|---|---|
| 180 | —CH₃ | 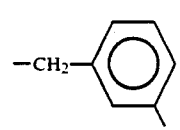 —CH₂—(3-Cl-phenyl) |  HO-tetrahydrofuranyl | O | O | —NH— | |
| 181 | —CH₃ | 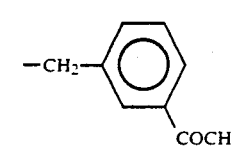 —CH₂—(3-COCH₃-phenyl) |  HO-tetrahydrofuranyl | O | O | —NH— | |
| 182 | —CH₃ | 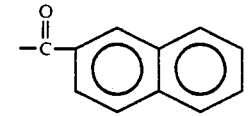 —CO—(2-naphthyl) |  HO-tetrahydrofuranyl | O | O | —NH— | |
| 183 | —CH₃ | 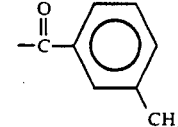 —CO—(3-CH₃-phenyl) |  HO-tetrahydrofuranyl | O | O | —NH— | |
| 184 | —CH₃ | 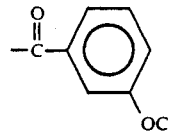 —CO—(3-OCH₃-phenyl) |  HO-tetrahydrofuranyl | O | O | —NH— | |
| 185 | —CH₃ | 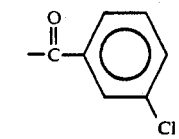 —CO—(3-Cl-phenyl) |  HO-tetrahydrofuranyl | O | O | —NH— | |
| 186 | —CH₃ | 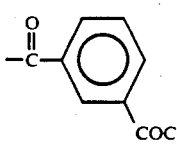 —CO—(3-COCH₃-phenyl) |  HO-tetrahydrofuranyl | O | O | —NH— | |
| 187 | —CH₃ | 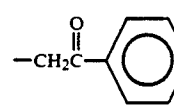 —CH₂CO—phenyl |  HO-tetrahydrofuranyl | O | O | —NH— | |
| 188 | —CH₃ | 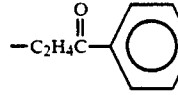 —C₂H₄CO—phenyl |  HO-tetrahydrofuranyl | O | O | —NH— | |

TABLE-1-continued

| Compound No. | R¹ | R² | R³ | X | Y | A | Melting point (°C.) |
|---|---|---|---|---|---|---|---|
| 189 | —CH₃ | —CH₂C(O)—C₆H₄(3-CH₃) | HO-CH₂-tetrahydrofuranyl | O | O | —NH— | |
| 190 | —CH₃ | —CH₂C(O)—C₆H₄(3-OCH₃) | HO-CH₂-tetrahydrofuranyl | O | O | —NH— | |
| 191 | —CH₃ | —CH₂C(O)—C₆H₄(3-Cl) | HO-CH₂-tetrahydrofuranyl | O | O | —NH— | |
| 192 | —CH₃ | —CH₂C(O)—C₆H₄(3-COCH₃) | HO-CH₂-tetrahydrofuranyl | O | O | —NH— | |
| 193 | —CH₃ | —O-naphthyl | HO-CH₂-tetrahydrofuranyl | O | O | —NH— | |
| 194 | —CH₃ | —S—C₆H₅ | HO-CH₂-tetrahydrofuranyl(OH,OH) | O | O | —NH— | |
| 195 | —CH₃ | —S—C₆H₅ | HO-CH₂-tetrahydrofuranyl(OH) | O | O | —NH— | |
| 196 | —CH₃ | —S—C₆H₅ | HO-CH₂-tetrahydropyranyl(OH,OH) | O | O | —NH— | |
| 197 | —CH₃ | —S—C₆H₅ | HO-CH₂-dioxolanyl | O | O | —NH— | |
| 198 | —CH₃ | —S—C₆H₅ | HO-CH₂-cyclopropyl | O | O | —NH— | |

TABLE-1-continued

[I]

| Compound No. | R¹ | R² | R³ | X | Y | A | Melting point (°C.) |
|---|---|---|---|---|---|---|---|
| 199 | —CH₃ | -S-C₆H₅ | HO-CH₂-CH(OH)-CH₂- (1,3-diol butyl) | O | O | —NH— | |
| 200 | —CH₃ | -S-C₆H₅ | HO-CH₂-CH(OH)-CH₂- (with HO groups) | O | O | —NH— | |
| 201 | —CH₃ | -S-C₆H₅ | HO-CH₂-C(CH₂OH)H-CH₂- | O | O | —NH— | |
| 202 | —CH₃ | -S-C₆H₅ | HO-CH₂-CH₂-C(OH)(CH₂-)- | O | O | —NH— | |

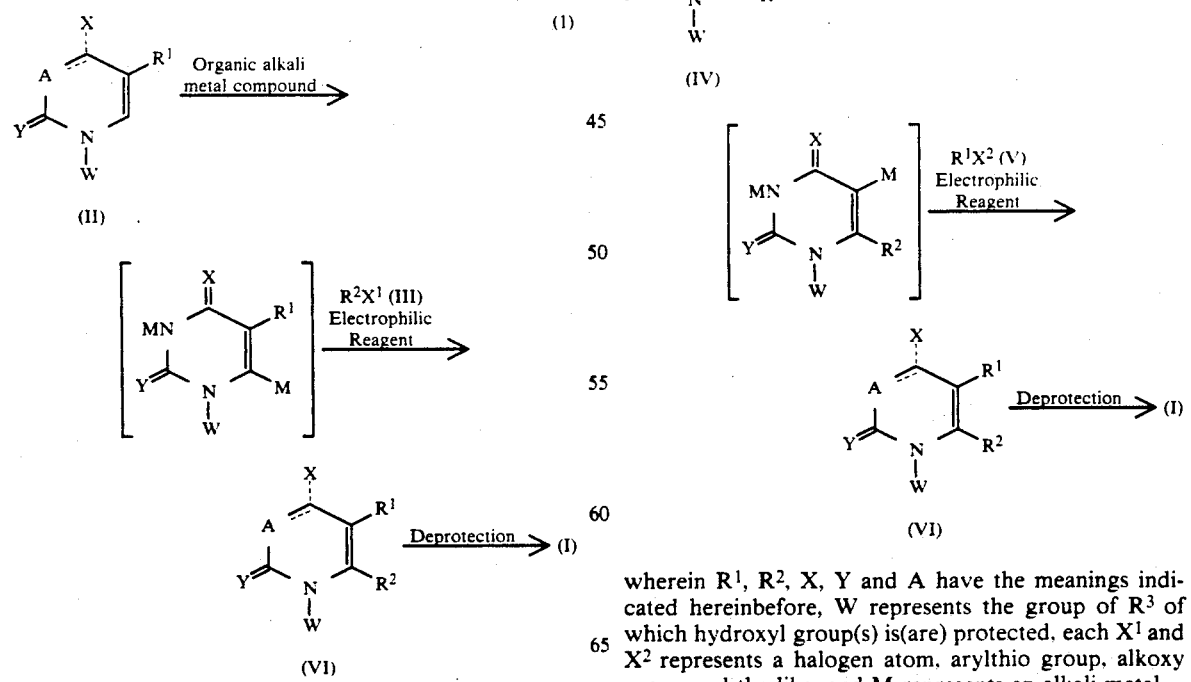

The compound of the invention may be preferably prepared in accordance with the following reaction formula (1) or (2);

wherein R¹, R², X, Y and A have the meanings indicated hereinbefore, W represents the group of R³ of which hydroxyl group(s) is(are) protected, each X¹ and X² represents a halogen atom, arylthio group, alkoxy group and the like, and M represents an alkali metal.

Any conventional protective group which does not dissociate under alkaline condition may be used for the group of W, i.e., the protection of the hydroxyl group of $R^3$.

Examples of such a protective group are an aralkyl group such as the benzyl group, trityl group, monomethoxytrityl group, dimethoxytrityl group and trimethoxytrityl group; a silyl group such as the trimethylsilyl group, triethylsilyl group, t-butyldimethylsilyl group, t-butyldiphenylsilyl group and dimethylphenylsilyl group; and a substituted alkyl group such as the tetrahydropyranyl group and methoxymethyl group. Among those protective groups, however, the silyl group is particularly preferred.

The compound of the general formula II or IV is firstly reacted with the organic alkali metal compound in a solvent, for example, an ether solvent such as diethyl ether and tetrahydrofuran, at a temperature of from $-80°$ C. to $-10°$ C. for 0.2 to 10 hours.

Examples of the organic alkali metal compound are potassium bistrimethylsilylamide, sodium bistrimetylsilylamide and lithium alkylamide, and lithium diisopropylamide (LDA) and lithium 2,2,6,6-tetramethylpiperidide (LTMP) are particularly preferable compounds. Such lithium alkylamides are preferably prepared immediately before the reaction. For example, lithium dialkylamide may be prepared by reacting a secondary amine such as diisopropylamine with an alkyl lithium such as n-butyl lithium in a solvent such as diethyl ether, dioxane, tetrahydrofuran and dimethoxyethane with agitation in the presence of an inert gas such as argon gas at $-80°$ C. to $-10°$ C. for 0.2 to 5 hours.

The organic alkali metal compound is generally used in an amount of 2 to 5 moles per mole of the compound represented by the formula II or IV.

Then, the electrophilic reagent of the general formula $R^2X^1$ or $R^1X^2$ is added in a ratio of about 1 to 5 moles to 1 mole of the compound of the formula II or IV to allow the reaction therewith under the same condition as in the reaction with the organic alkali metal compound.

The electrophilic reagents should be those having a group of $R^1$ or $R^2$ defined above. Possible examples of the electrophilic reagents are diaryl disulfide, arylsulfenyl chloride, dialkyl disulfide, dicycloalkyl disulfide, alkyl halide, aralkyl halide such as benzyl bromide, organic acid halide such as benzoyl halide and isobutyroyl halide, acid anhydride and ester thereof, arylcarbonylalkyl halide such as phenacyl chloride and the like.

The starting material of the compound represented by the general formula II or IV can be prepared by a conventional method. For example, the compound of the general formula II may be obtained by condensing a trimethylsilylated uracil derivative with (2-acetoxyethoxy)methyl bromide, hydrolyzing the resulting condensate and protecting with one of the protective groups mentioned above. See Can. J. Chem., 60, 547 (1982) and the like for the details.

The protection of the hydroxyl group with the protection group can be also carried out by a conventional method. For example, the hydroxyl group may be protected with a silyl group by reacting the compound having the hydroxyl group with 1 to 10 times by mole of silylating reagent such as trimethylsilyl chloride and t-butyldimetylsilyl chloride at a temperature of from 0° C. to 50° C. in a solvent such as pyridine, picoline, diethylaniline, dimethylaniline, triethylamine, dimethylformamide, acetonitrile, tetrahydrofuran and a mixture composed of any combination of these solvents.

The compound of the general formula IV can be prepared in accordance with the reaction formula (1) using a compound of the formula II having a hydrogen atom as the group of $R^1$.

Then, the protective group may be eliminated from the thus obtained compound of the general formula VI. This elimination of the protective group may be carried out after separation or purification of the nucleoside by means of a conventional method such as recrystallization, adsorption and ion-exchange chromatography, if desired.

The elimination of the protective group can be carried out by a conventional method according to the kind of the protective group, for example, by hydrolysis, treatment with ammonium fluoride or catalytic reduction.

The resulting compound of the present invention represented by the general formula I can be separated and purified by an appropriate conventional method such as recrystallization, adsorption or ion-exchange chromatography.

The compounds having a nitro group on the benzene ring obtained in the reaction of formula (1) or (2) can be converted to compounds having an amino group by hydrogenation in accordance with the reaction formula (3) below. The hydrogenation can be carried out in a solvent such as alcohol and acetic acid in the presence of a catalyst such as palladium/carbon at an appropriate temperature of from room temperature to 80° C.:

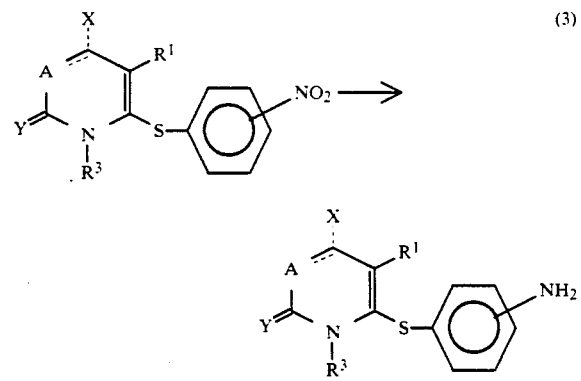

(3)

wherein the symbols have the same meanings as indicated above.

The compounds having an arylthio group, alkylthio group or cycloalkylthio group can be converted to corresponding compounds having an aryl sulfoxide group, alkyl sulfoxide group or cycloalkyl sulfoxide group by using an oxidation agent such as hydrogen peroxide and m-chloroperbenzoic acid in accordance with the reaction formula (4) below:

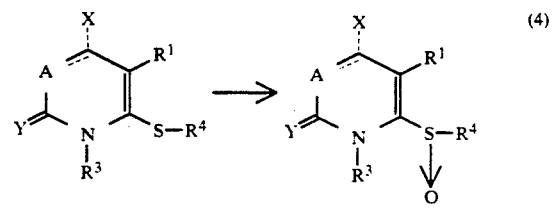

(4)

wherein R[4] represents an aryl, alkyl or cycloalkyl group and the other symbols have the same meanings as indicated above.

The compounds having phenyl sulfoxide group can be converted to the corresponding compounds having an arylthio group by reacting with sodium aryloxide or sodium arylthiolate in an organic medium such as tetrahydrofuran, alcohol, dimethylformamide and acetonitrile at an appropriate temperature of from room temperature to 100° C. in accordance with the reaction formula (5) below:

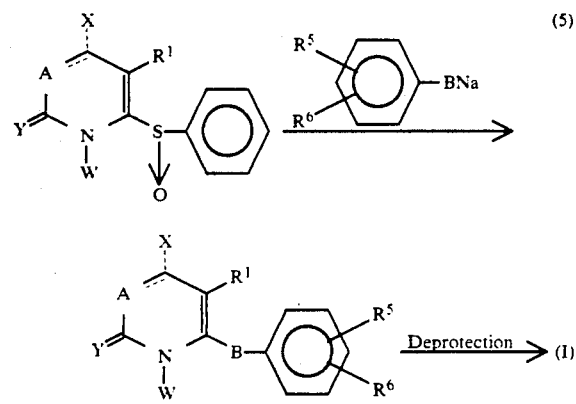

(5)

wherein B represents a sulfur or oxygen atom, R[5] and R[6] independently represent a halogen atom such as chlorine, bromine, fluorine and iodine atom, alkyl group such as methyl, ethyl, propyl and butyl group, halogenated alkyl group such as trichloromethyl group, alkoxy group such as methoxy, ethoxy, propoxy and butoxy group, hydroxyl group, nito group, amino group, cyano group or acyl group such as acetyl group, and the other symbols have the same meanings as indicated above.

The compounds according to the present invention can be also prepared in accordance with the reaction formula (6) or (7) below:

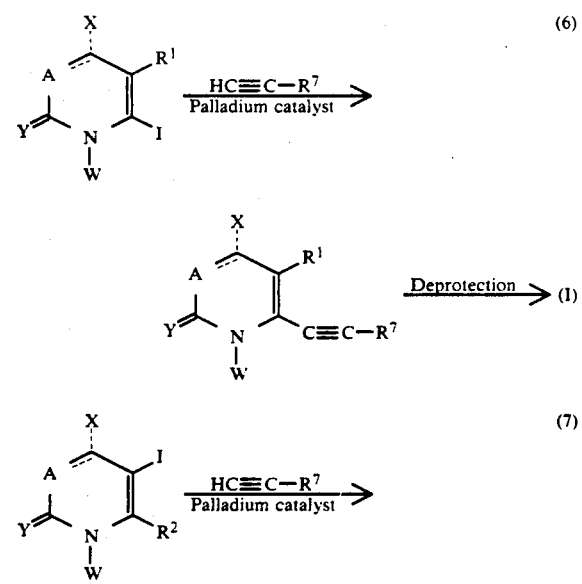

(6)

(7)

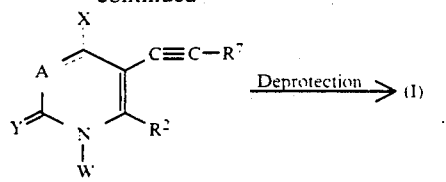

wherein R[7] represents an alkyl group such as methyl and ethyl group, aryl group such as phenyl and tolyl group or a protective silyl group, and the other symbols have the same meanings as indicated above.

The reactions of the formulae (6) and (7) can be carried out in an amine solvent such as diethylamine and triethylamine in the presence of a palladium catalyst at an appropriate temperature of from room temperature to 70° C. The reactions may be carried out more homogeneously by adding another solvent such as acetonitrile to the reaction mixture.

As the catalyst, a palladium catalyst of bis(triphenylphosphine)palladium dichloride, tetrakis(triphenylphosphine)palladium(0) and bis(diphenylphosphino)ethanepalladium dichloride can be used in combination with cuprous iodide.

The compounds of the present invention can be also prepared in accordance with the reaction formula (8) or (9) below, and the said reactions can be carried out in a similar manner to the reactions of the formulae (6) and (7) except that an olefin derivative of $H_2C=CH-R^8$ wherein R[8] represents an alkoxycarbonyl, nitrile, carbamoyl group or the like is used instead of the acetylene derivative in the reactions of formulae (6) and (7):

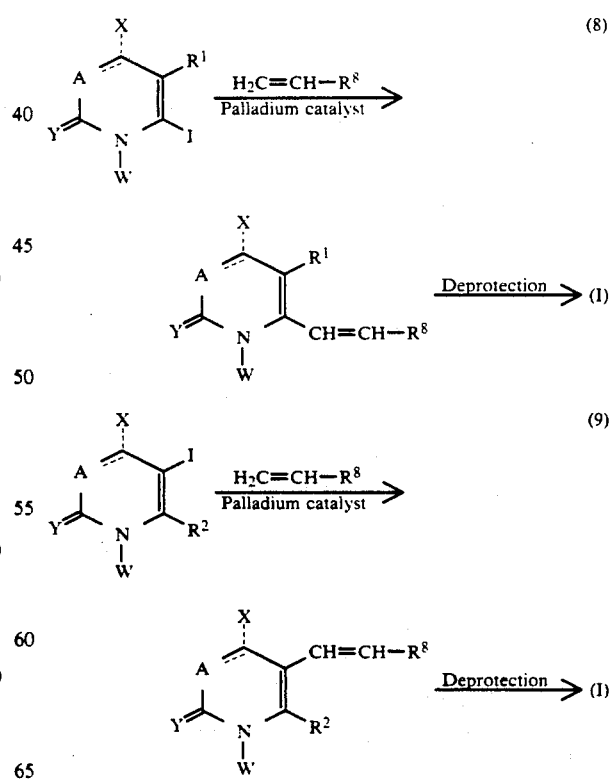

(8)

(9)

wherein the symbols have the same meanings as indicated above.

The reactions of the formulae (8) and (9) can be carried out by using the same palladium catalyst as used in the reactions of the formulae (6) and (7).

The compounds according to the invention can be also prepared in accordance with the reaction formula (10) below:

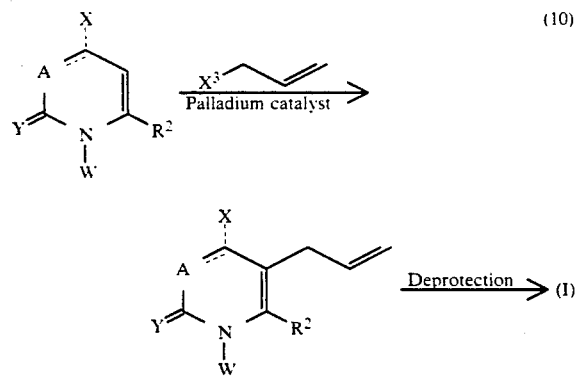
(10)

wherein $X^3$ represents a halogen atom such as chlorine, bromine and iodine, and the other symbols have the same meanings as indicated above.

The compounds according to the invention can be also prepared in accordance with the reaction formula (11) or (12) below:

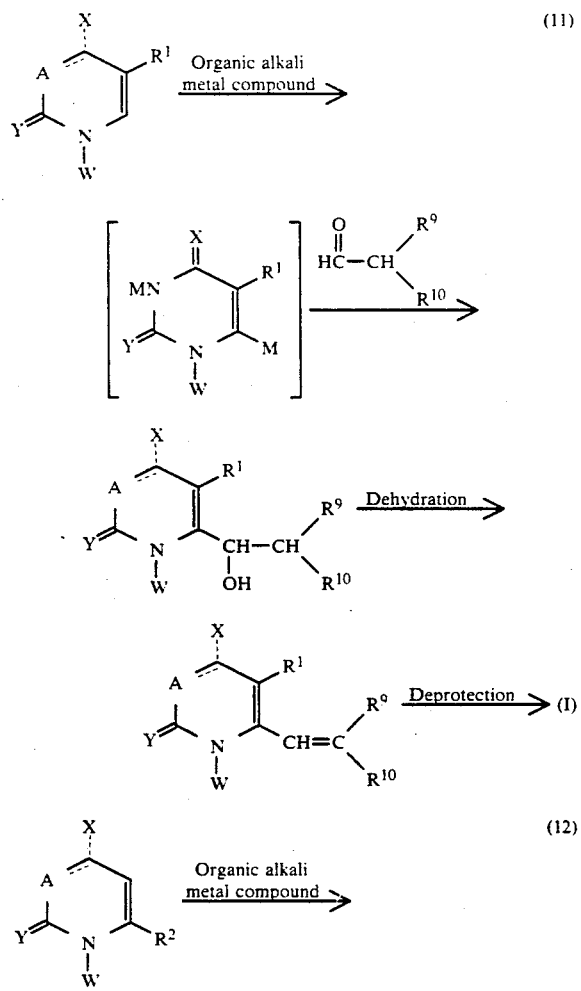

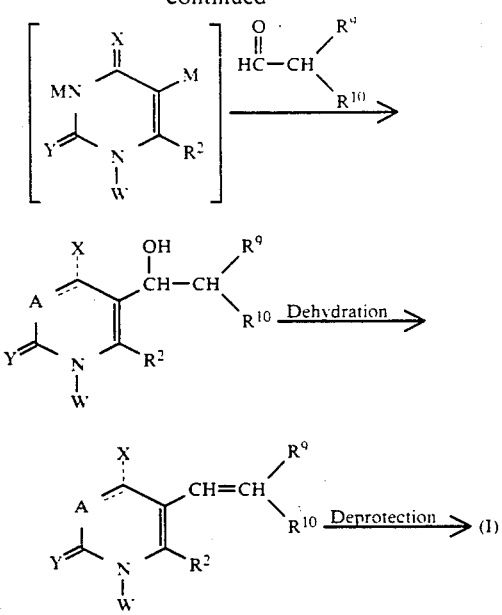

wherein the symbols have the same meanings as indicated above.

In the reactions of the formulae (11) and (12), the compounds of the present invention having an alkenyl group are prepared by dehydrating an intermediate compound by means of an dehydrating agent such as mesyl chloride, tosyl chloride and thionyl chloride to produce the alkenyl group, the intermediate compound being prepared in accordance with the reaction formulae (1) and (2) as described hereinbefore except that a compound of

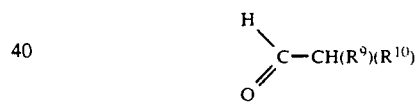

wherein $R^9$ and $R^{10}$ independently represent a hydrogen atom, alkyl group such as methyl, ethyl and propyl group or aryl group such as phenyl group is used instead of the compounds $R^1X^2$ and $R^2X^1$, compounds R By hydrogenation, the alkynyl group of the compounds produced in the reactions of the formulae (6) and (7) can be converted to the corresponding alkenyl group or alkyl group and the alkenyl group of the compounds produced in the reactions (8) to (12) can be converted to the corresponding alkyl group. For the reduction into an alkenyl group, the hydrogenation may be carried out at an appropriate temperature of from room temperature to 80° C. under hydrogen atmosphere in the presence of a catalyst such as palladium/barium sulfate, palladium/calcium carbonate, palladium/calcium carbonate/lead acetate and palladium/barium sulfate/quinoline in a solvent such as alcohol and acetic acid. For the reduction into an alkyl group, the hydrogenation may be carried out by using a catalyst such as palladium/carbon and palladium hydroxide under the same conditions used for producing the alkenyl group.

The 6-substituted acyclouridine and acyclothymidine derivatives obtained in the above described reactions can be converted into 4-thio derivatives by heating with 2,4-bis(4-methoxyphenyl)-1,3-dithia-2,4-diphosphetane 2,4-disulfide in a solvent such as toluene and xylene in accordance with the reaction formula (13) below.

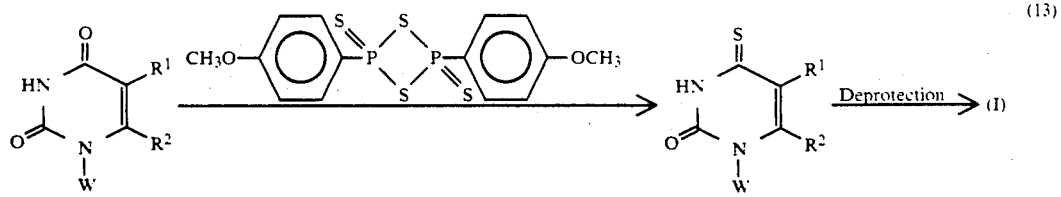

wherein the symbols have the same meanings as indicated above.

The 4-thio derivatives can be also obtained by reacting a 4-chloro derivatives with sodium bisulfide, the 4 chloro derivatives being obtained by the chlorination of the uridine or thymidine derivatives by means of chlorinating agent such as phosphorus pentachloride or phosphorus oxychloride.

Further, 4-amino derivatives can be prepared by reacting the acyclouridine or thymidine derivative with 1-(2-mesitylenesulfonyl)-3-nitro-1,2,4-triazole in the presence of diphenylphosphoric acid in a solvent such as pyridine to produce a corresponding 4-(3-nitro-1,2,4-triazole) derivative and then reacting the obtained triazole derivative with ammonia by an addition of aqueous ammonia at an appropriate temperature of from room temperature to 100° C. in accordance with the reaction formula (14) below:

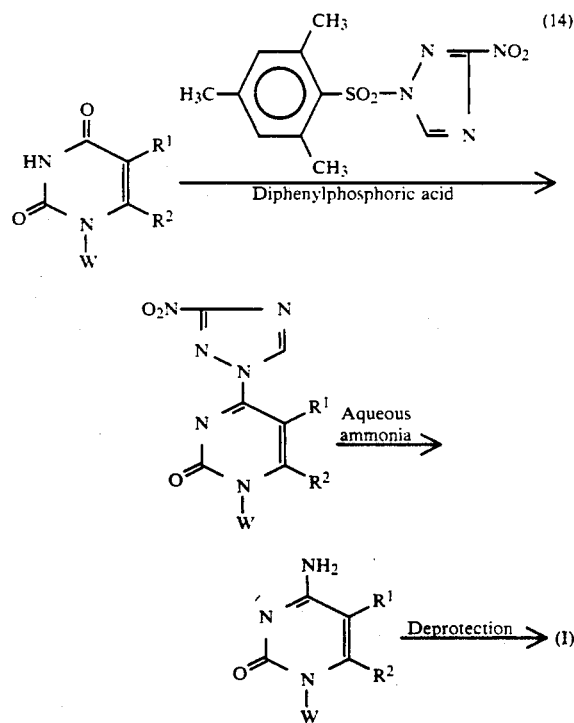

wherein the symbols have the same meanings as indicated above.

The acyclopyrimidine derivative according to the present invention may be used in the form of a pharmaceutically acceptable salt produced by a conventional method, the said salt being, for example, an alkali metal salt such as the sodium or potassium salt, alkaline earth metal salt such as the magnesium salt, ammonium salt or alkylammonium salt such as methylammonium, dimethylammonium, trimethylammonium or tetramethylammonium salt thereof.

The compound according to the invention can be administered to human beings via any route, oral, rectal, parenteral or local. The administration dose of the compound according to the invention may be determined according to age, physical condition, body weight and the like of a patient to be treated; however, a suitable daily dose of the compound is 1 to 100 mg/(body weight) kg, preferably 5 to 50 mg/(body weight)kg and it is administered one to several times.

The compounds of the present invention are generally prepared in a pharmaceutical composition with suitable carrier, excipient and other additives. Either liquid carrier or solid carrier may be suitably used for the present antiviral agent.

Examples of the solid carrier are lactose, kaolin, sucrose, crystalline cellose, corn starch, talc, agar, pectin, stearic acid, magnesium stearate, lecithin, sodium chloride and the like.

Examples of the liquid carrier are glycerin, peanut oil, polyvinyl pyrrolidone, olive oil, ethanol, benzyl alcohol, propylene glycol, water and the like.

The present antiviral agent may be made in various forms. For example, it may be in a form of a tablet, powder, granule, capsule, suppository, troche or the like when a solid carrier is used, and it may be also in a form of a syrup, emulsion, soft gelatin capsule, cream, gel, paste, spray, injection solution or the like when a liquid carrier is used.

The novel 6-substituted acyclopyrimidine nucleoside derivatives according to the present invention have an effective antiviral activity against a virus such as a retrovirus and have a relatively low toxicity against the host cell, hence the derivatives of the invention are extremely useful as an active ingredient of an antiviral agent.

EXAMPLES

The invention will be further illustrated hereafter by way of examples, but these examples do not limit the invention and many variations and modifications can be made without departing from the scope of the present invention.

REFERENCE EXAMPLE 1

Production of 1-[(2-t-butyldimethylsilyloxyethoxy)-methyl]thymine (a compound of the general formula II wherein $R^1$=CH$_3$, W=2-t-butyldimethylsilyl(TBDMS)-O(CH$_2$)$_2$—O—CH$_2$—, A=—NH— and X=Y=O)

To 476 mg (2.38 mmol) of 5-methylacyclouridine, 580 mg (4.18 mmol) of t-butyldimethylsilyl chloride and 556 mg (8.17 mmol) of imidazole were added. The mixture was dissolved in 10 ml of dimethylformamide and the solution was stirred to allow the reaction overnight, The reaction solution was distributed between 200 ml of water and 200 ml of ethyl acetate. The ethyl acetate layer was taken up and concentrated under a reduced pressure. The residue was adsorbed on 30 g of silica gel, washed with benzene and eluted with 10% methanol/chloroform. The eluate was concentrated under reduced pressure and then crystallized from water/ethanol to obtain 672 mg of the target compound (Yield: 90%).

Melting point: 137° to 138° C.

EXAMPLE 1

(1) Production of 1-[(2-t-butyldimethylsilyloxyethoxy)methyl]-6-phenylthiothymine (a compound of the general formula VI wherein $R^1 = CH_3$,

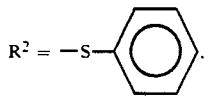

$W = TBDMS—O—CH_2CH_2—O—CH_2—$,
$A = —NH—$ and $X = Y = O$)

After cooling 10 ml of tetrahydrofuran to −70° C., 0.263 ml (1.86 mmol) of diisopropylamine and 1.86 mmol of n-butyllithium were succesively added thereto in the presence of an argon flow to obtain a lithium diisopropylamide solution. Separately, 229 mg (0.73 mmol) of 1-[(2-t-butyldimethylsilyloxyethoxy)methyl]thymine was dissolved in 5 ml of tetrahydrofuran and added dropwise to the lithium diisopropylamide solution for effecting the reaction at −70° C. for 1 hour. A solution of 332 mg (1.52 mmol) of diphenyl disulfide in 5 ml of tetrahydrofuran was added to dropwise to the reaction solution while maintaining the latter at −70° C. and the reaction kept for 1 hour. After the reaction, 0.2 ml of acetic acid was added to the reaction solution and the temperature of the solution was allowed to revert to room temperature. The resultant solution was distributed between chloroform and saturated aqueous sodium hydrogencarbonate solution. The chloroform layer was concentrated and evaporated to dryness. The residue was dissolved in a small amount of chloroform, adsorbed on a silica gel column and eluted with chloroform to obtain 226 mg of the target compound (Yield: 73%).

Melting point: 89° to 90° C.

(2) Production of 1-[(2-hydroxyethoxy)methyl]-6-phenylthiothymine (Compound No.1)

An amount of 98 mg of 1-[(2-t-butyldimethylsilyloxyethoxy)methyl]-6-phenylthiothymine obtained in the process (1) was dissolved in 2 ml of tetrahydrofuran, added to 2 ml of acetic acid and 1 ml of water and allowed to react at room temperature overnight. The reaction solution was concentrated to dryness under reduced pressure, adsorbed on a silica gel (20 g) column and eluted with 1% methanol/chloroform. The eluate was concentrated and crystallized from ethyl acetate/methanol to obtain 65 mg of the target compound (Yield: 91%).

Melting point: 123° to 124° C.

EXAMPLES 2 to 5

An acyclouridine derivative having a protecting group and represented by the general formula II wherein $R^1 = F$, Cl, Br or H, $W = TBDMS—O—CH_2CH_2—O—CH_2—$, $A = —NH—$ and $X = Y = O$) were obtained in the same way as in Example 1 and treated in the same way as Example 1 to produce Compounds No. 2 to 5 in Table 1.

EXAMPLES 6 to 27

Using various disulfide derivatives in place of diphenyl disulfide in Example 1, Compounds No. 6 to 20 and 22 to 28 in Table 1 were obtained in the same way as in Example 1 (1) and (2).

EXAMPLE 28

Production of 1-[(2-hydroxyethoxy)methyl]-6-(4-acetylphenyl-1-thio)thymine (Compound No. 20)

(1) An amount of 576 mg (1.37 mmol) of 1-[(2-t-butyldimethylsilyloxyethoxy)methyl]-6-phenylthiothymine was dissolved in 10 ml of chloroform and to this solution 235 mg (1.37 mmol) of m-chloroperbenzoic acid was added to react for 20 hours at room temperature. After the reaction, the reaction mixture was concentrated to dryness. The residue was dissolved in a small amount of chloroform, adsorbed on a silica gel column and eluted with 10% n-hexane/chloroform. The eluate was concentrated to dryness to yield 177 mg of 1-[(2-t-butyldimethylsilyloxyethoxy)methyl]thymine-6-yl-phenyl sulfoxide (Yield 40%).

(2) An amount of 39 mg (0.25 mmol) of 4-acetylthiophenol was dissolved in 2 ml of tetrahydrofuran and to this solution 0.25 mmol of sodium hydride was added to react for 1 hour at room temperature. To the reaction solution, 87.5 mg (0.2 mmol) of 1-[(2-t-butyldimethylsyliloxyethoxy)methyl]thymine-6-yl-phenyl sulfoxide was added and allowed to react under a reflux for 2 days. The obtained reaction solution was then added to 5 ml of acetic acid, 3 ml of tetrahydrofuran and 1.5 ml of water and allowed to react overnight at room temperature. The resultant solution was concentrated to dryness, and the residue was dissolved in a small amount of chloroform, adsorbed on a silica gel column and eluted with 3% methanol/chloroform. The eluate was concentrated and dried to obtain 42 mg of the target compound (Yield 61%).

Melting point 107° to 108° C.

EXAMPLE 29

Production of 1-[(2-hydroxyethoxy)methyl]-6-(6-hydroxynaphthyl 2-thio)thymine (Compound No. 29)

An amount of 314 mg (1 mmol) of 1-[(2-t-butyldimethylsilyloxyethoxy)methyl]thymine was reacted with 1.16g (2 mmol) of 2,2'-t-butyldimethylsilyloxy-6,6'-dinaphthyl disulfide as in Example 1 (1). Then the resultant solution was treated as in Example 1 (2) to obtain 1-[(2-hydroxyethoxy)methyl]-6-(6-t-butyldimethylsilyloxynaphthyl-2-thio)thymine, which was then dissolved in 37 ml of tetrahydrofuran, added to 1 ml of water and 2 ml of 1M tetrabutylammonium fluoride/tetrahydrofuran solution and allowed to react for 30 minutes at room temperature. After the reaction, the resultant solution was concentrated to dryness. The residue was dissolved in a small amount of chloroform, adsorbed on a silica gel column. eluted with 5% methanol/chloroform. The eluate was concentrated and crystallized from ethyl acetate to obtain 315 mg of the target compound (Yield: 42.8%).

Melting point: 188° C.

EXAMPLES 30 to 34

Using the following compounds in place of 1-[(2-t-butyldimethylsilyloxyethoxy)methyl]thymine in Example 1, Compounds No. 30 to 34 in Table 1 were obtained in the same manner as Example 1 (1) and (2):

1-[(3-t-butyldimethylsilyloxypropoxy)methyl]thymine;
1-[(2-t-butyldimethylsilyloxy-1-methylethoxy)methyl]thymine;
1-[(2-t-butyldimethylsilyloxy-1-t-butyldimethylsilyloxymethylethoxy)methyl]thymine;
1-[2,3-di-t-butyldimethylsilyloxypropoxy)methyl]thymine; and
1-[1-(2-t-butyldimethylsilyloxyethoxy)ethyl]uracil.

EXAMPLE 35

Production of 1-[(2-hydroxyethoxy)methyl]-6-(2-aminophenyl-1-thio)thymine (Compound No. 35)

An amount of 200 mg (0.57 mmol) of 1-[(2-hydroxyethoxy)methyl]-6-(2-nitrophenyl-1-thio)thymine (Compound No. 16) was dissolved in 12 ml of acetic acid and 5 ml of ethanol, was added to 50 mg of 5% palladium/carbon and allowed to react at room temperature for 6 hours under 1 atm of hydrogen atmosphere. After removing the palladium/carbon by filtration, the reaction solution was concentrated to dryness. The residue was crystallized from toluene/ethanol to obtain the target compound.

Melting point: 140° C.

EXAMPLE 36

Production of 1-[(2-hydroxyethoxy)methyl]-6-(3-aminophenyl-1-thio)thymine (Compound No. 36)

In place of 1-[(2-hydroxyethoxy)methyl]-6-(2-nitrophenyl-1-thio)thymine in Example 35, 1-[(2-hydroxyethoxy)methyl]-6-(3-nitrophenyl-1-thio)thymine was reacted and treated similarly to obtain the target compound.

Melting point: 235° to 238° C.

EXAMPLE 37

Production of 1-[(2-hydroxyethoxy)methyl]thymine-6-yl-phenyl sulfoxide (Compound No. 37)

An amount of 100 mg of 1-[(2-hydroxyethoxy)methyl]-6-phenylthiothymine was dissolved in 2 ml of acetic acid and 3 ml of ethanol, was added to 0.7 ml of 30% hydrogen peroxide solution and allowed to react at room temperature for one week. Then the resultant was distributed between ethyl acetate and aqueous layers, and the ethyl acetate layer was concentrated to dryness. The residue was crystallized from ethanol/toluene to obtain 28.3 mg of the target compound (Yield: 26.5%).

Melting point: 130° C.

EXAMPLE 38

Production of 1-[(2-hydroxyethoxy)methyl]-6-(2-phenyl-ethynyl)thymine (Compound No. 38)

(1) An amount of 3.14 g (10 mmol) of 1-[(2-t-butyldimethylsilyloxyethoxy)methyl]thymine was treated in the same way as in Example 1 (1) except that 20 mmol iodine was used instead of diphenyl disulfide to obtain 3.11 g of 1-[(2-t-butyldimethyl silyloxyethoxy)methyl]-6-iodothymine (Yield: 70.6%)

(2) An amount of 440 mg (1 mmol) of 1-[(2-t-butyldimethylsilyloxyethoxy)methyl]-6-iodothymine obtained in process (1) was dissolved in 10 ml of triethylamine and 3 ml of acetonitrile, and was added to 70.2mg bis(triphenylphosphine)palladium dichloride. 19 mg of cuprous iodide and 0.33 ml of phenylacetylene and allowed to react at 60° C. for 1.5 hours. After the temperature of the reaction solution had reverted to room temperature, the solution was concentrated to dryness. The residue was then distributed between chloroform and aqueous layers, and the chloroform layer was concentrated to dryness. The residue was dissolved in a small amount of chloroform, adsorbed on a silica gel column and eluted with 30% n-hexane/chloroform. After concentrating the eluate, the residue was dissolved in 5ml tetrahydrofuran, to which 5 ml of acetic acid and 2.5 ml of water were added to react overnight at room temperature. The reaction solution was concentrated and crystallized from toluene/ethanol to obtain 250 mg of the target compound (Yield: 84%).

Melting point: 214° C.

EXAMPLE 39

Production of 1-[(2-hydroxyethoxy)methyl]-6-(1-propynyl)thymine (Compound No. 39)

Using methylacetylene in place of phenylacetylene in Example 38 (2), the target compound was obtained in the same manner as in Example 38 (Yield: 53%).

Melting point: 169° C.

EXAMPLE 40

Production of 1-[(2-hydroxyethoxy)methyl]-6-ethynylthymine (Compound No. 40)

In place of phenylacetylene in Example 38 (2), 0.82 ml (6 mmol) of trimethylsilylacetylene was used to react with 880 mg (2 mmol) of 1-[(2-t-butyldimethylsilyloxyethoxy)methyl]-6-iodothymine for producing 1-[(2-hydroxyethoxy)methyl]-6-(2-trimethylsilylethynyl)thymine in the same manner as Example 38 (2). The obtained compound was dissolved in 100ml of methanol, was added to 1 ml of 1N sodium hydroxide aqueous solution and allowed to react for two minutes at room temperature. Then the reaction solution was neutralized with hydrochloric acid and concentrated. The resultant was distributed between ethyl acetate and aqueous layers, and the ethyl acetate layer then concentrated to dryness. The residue was crystallized from toluene/ethanol to obtain 170 mg of the target compound (Yield: 38%).

Melting point: 154° C.

EXAMPLE 41

Production of 1-[(2-hydroxyethoxy)methyl]-6-(2-phenylvinyl)thymine (Compound No. 41)

An amount of 120 mg (0.4 mmol) of 1-[(2-hydroxyethoxy)methyl]-6-(2-phenylethynyl)thymine (Compound No. 38) was dissolved in 15 ml of ethanol and 3 ml of acetic acid, was added to 17 mg of 10% palladium/barium sulfate and stirred for two minutes at room temperature under a hydrogen atmosphere of 1 atm. After completion of the reaction, the palladium/barium sulfate was filtered off from the reaction solution, and then the filtrate was concentrated to dryness. The residue was crystallized from toluene to obtain 106 mg of the target compound (Yield: 88%).

Melting point: 114° C.

EXAMPLE 42

Production of 1-[(2-hydroxyethoxy)methyl]-6-(1-propenyl)thymine (Compound No. 42)

In place of Compound No. 38 in Example 41, 1-[(2-hydroxyethoxy)methyl]-6-(1-propynyl)thymine (Compound No. 39) was used in the same reaction as Example 41 to obtain the target compound.
Melting point: 97° C.

EXAMPLE 43

Production of 1-[(2-hydroxyethoxy)methyl]-6-vinylthymine (Compound No. 43)

In place of Compound No. 38 in Example 41, 1-[(2-hydroxyethoxy)methyl]-6-ethynylthymine (compound No. 40) was used in the same reaction as Example 41 to obtain the target compound.
Melting point: 114° C.

EXAMPLE 44

Production of 1-[(2-hydroxyethoxy)methyl]-5-iodo-6-phenylthiouracil (Compound No. 44)

(1) After cooling 35 ml of tetradydrofuran to −70° C., 2.1 g (15 mmol) of 2,2,6,6-tetramethylpiperidine and 15 mmol of n-butyl lithium were successively added thereto to obtain a lithium tetramethylpiperidide solution. Separately, 2.04 g (15 mmol) of 1-[(2-t-butyldimethylsilyloxyethoxy)methyl]-6-phenylthiouracil was dissolved in 20 ml of tetrahydrofuran and added dropwise to the said lithium tetramethylpiperidide solution to react for an hour at −70° C. Then, a solution of 3.81 g (15 mmol) of iodine in 20 ml of tetrahydrofuran was further added to the reaction solution while maintaining the reaction temperature at −70° C. to react for an hour. After the completion of the reaction, the reaction solution was added to 0.8 ml of acetic acid, allowed to warm to room temperature and distributed between a chloroform layer and a saturated aqueous solution of sodium bicarbonate. The chloroform layer was concentrated to dryness. The residue was crystallized from petroleum ether to obtain 1.835 g of 1-[(2-t-butyldimethylsilyloxyethoxy)methyl]-5-iodo-6-phenylthiouracil (Yield: 62.8%).
Melting point: 84° to 85° C.

(2) 1-[(2-t-butyldimethylsilyloxyethoxy)methyl]-5-iodo-6-phenylthiouracil obtained in the above process (1) was reacted and treated in the same manner as Example 1 (2) to obtain the target compound.
Melting point: 180° to 182° C.

EXAMPLE 45

Production of 1-[(2-hydroxyethoxy)methyl]-5-(2-phenylethynyl)-6-phenylthiouracil (Compound No. 45)

In place of 1-[(2-t-butyldimethylsilyloxyethoxy)methyl]-6-iodothymine in Example 38 (2), 1-[(2-t-butyldimethylsilyloxyethoxy)methyl]-5-iodo-6-phenylthiouracil was used in the same reaction and treatment as in Example 38 except that the crystallization was carried out from ethyl acetate to obtain the target compound.
Melting point: 146° to 148° C.

EXAMPLE 46

Production of 1-[(2-hydroxyethoxy)methyl]-5-(1-propynyl)-6-phenylthiouracil (Compound No. 46)

In place of phenylacetylene in Example 45, methylacetylene was reacted and treated under the same condition to obtain the target compound.
Melting point: 165° to 166.5° C.

EXAMPLE 47

Production of 1-[(2-hydroxyethoxy)methyl]-5-ethynyl-6-phenylthiouracil (Compound No. 47)

By repeating the procedures of Example 40 except that 1-[(2-t-butyldimethylsilyloxyethoxy)methyl]-5-iodo-6-phenylthiouracil was used in place of 1-[(2-t-butyldimethylsilyloxyethoxy)methyl]-6-iodothymine, 1-[(2-t-butyldimethylsilyloxyethoxy)methyl]-5-(2-trimethylsilylethynyl)-6-phenylthiouracil was obtained. The obtained compound was dissolved in tetrahydrofuran and desilylated with tetrabutylammonium fluoride to obtain the target compound.
Melting point: 163° to 165° C.

EXAMPLE 48

Production of 1-[(2-hydroxyethoxy)methyl]-5-(2-phenylvinyl)-6-phenylthiouracil (Compound No. 48)

In place of 1-[(2-hydroxyethoxy)methyl]-6-(2-phenylethynyl)thymine in Example 41, 1-[(2-hydroxyethoxy)methyl]-5-(2-phenylethynyl)-6-phenylthiouracil was subjected to the same reaction for two days and the same treatment as in Example 41 except that the crystallization was carried out from ethyl acetate/n-hexane to obtain the target compound.
Melting point: 141° to 145° C.

EXAMPLE 49

Production of 1-[(2-hydroxyethoxy)methyl]-5-(1-propenyl)-6-phenylthiouracil (Compound No. 49)

In place of 1-[(2-hydroxyethoxy)methyl]-6-(2-phenylethynyl)thymine in Example 41, 1-[(2-hydroxyethoxy)methyl]-5-(1-propynyl)-6-phenylthiouracil was subjected to the same reaction and treatment as in Example 41 except that the crystallization was carried out from isopropyl ether to obtain the target compound.
Melting point: 76° to 77° C.

EXAMPLE 50

Production of 1-[(2-hydroxyethoxy)methyl]-5-vinyl-6-phenylthiouracil (Compound No. 50)

In place of 1-[(2-hydroxyethoxy)methyl]-6-(2-phenylethynyl)thymine in Example 41, 1-[(2-hydroxyethoxy)methyl]-5-ethynyl-6-phenylthiouracil was subjected to the same reaction and treatment as in Example 41 except that the crystallization was carried out from ethyl acetate/n-hexane to obtain the target compound.
Melting point: 100° to 103° C.

EXAMPLE 51

Production of 1-[(2-hydroxyethoxy)methyl]-5-benzyl-6-phenylthiouracil (Compound No. 51)

The same reaction and treatment as in Example 44 were effected except that benzyl bromide was used in place of iodine and that the crystallization was carried out from isopropyl ether to obtain the target compound.
Melting point: 126° to 128° C.

EXAMPLE 52

Production of 1-[(2-hydroxyethoxy)methyl]-5,6-diphenylthiouracil (Compound No. 52)

The same reaction and treatment as in Example 44 were effected except that diphenyl disulfide was used in place of iodine and that the crystallization was carried out from toluene to obtain the target compound.
Melting point: 146° to 148° C.

EXAMPLE 53

Production of 1-[(2-hydroxyethoxy)methyl]-5-benzoyl-6-phenylthiouracil (Compound No. 53)

The same reaction and treatment as in Example 44 were effected except that benzoyl chloride was used in place of iodine and that the crystallization was carried out from ethyl acetate to obtain the target compound.
Melting point: 150° to 151° C.

EXAMPLE 54

Production of 1-[(2-hydroxyethoxy)methyl]-5-isobutyroyl-6-phenylthiouracil (Compound No. 54)

The same reaction and treatment as in Example 44 were effected except that isobutyroyl chloride was used in place of iodine and that the crystallization was carried out from ethyl acetate to obtain the target compound.
Melting point: 144° to 145° C.

EXAMPLE 55

Production of 1-[(2-hydroxyethoxy)methyl]-5-phenacyl-6-phenylthiouracil (Compound No. 55)

The same reaction and treatment as in Example 44 were effected except that phenacyl bromide was used in place of iodine and that the crystallization was carried out from ethyl acetate to obtain the target compound.
Melting point: 151.5° to 153.5° C.

EXAMPLE 56

Production of 1-[(2-hydroxyethoxy)methyl]-6-phenylthiocytosine (Compound No. 56)

An amount of 200 mg (0.49 mmol) of 1-[(2-t-butyldimethylsilyloxyethoxy)methyl]-6-phenylthiouracil was dissolved in 1.3 ml of pyridine, was added to 727 mg (2.45 mmol) of 2,4,6-trimethylbenzene-1-sulfonyl-(3-nitro-1,2,4-triazole) and 61.3 mg (0.245 mmol) of 1,1-diphenylphosphoric acid and allowed to react for overnight. Then, the resultant solution was added to 1 ml of water and 1 ml of ethanol, left at room temperature for 20 minutes, concentrated to dryness. The residue was then dissolved in a small amount of chloroform, adsorbed on a silica gel column and eluted with 30% hexane/chloroform, and the eluate was concentrated. The residue was then dissolved in 5 ml dioxane, was added to 3 ml of concentrated aqueous ammonia and allowed to react at room temperature for 30 minutes. The reaction solution was concentrated to dryness. The residue was dissolved in a small amount of chloroform, adsorbed on a silica gel column and eluted, with 4% methanol/chloroform. The eluate was concentrated, and the resulting residue was then dissolved in 1 ml of tetrahydrofuran, was added to 1 ml of acetic acid and 0.5 ml of water and left to react at room temperature overnight. After evaporating to dryness, the resulting solid was crystallized from ethanol to obtain 70.3 mg of the target compound (Yield: 49%).
Melting point: 202° C.

EXAMPLE 57

Production of 1-[(2-hydroxyethoxy)methyl]-5-methyl-6-phenylthiocytosine (Compound No. 57)

The same reaction and treatment as in Example 56 was carried out except that 1-[(2-t-butyldimethylsilyloxyethoxy)methyl]-6-phenylthiothymine was used in place of 1-[(2-t-butyldimethylsilyloxyethoxy)methyl]-6-phenylthiouracil to obtain the target compound. The crystallization was carried out from ethanol.
Melting point: 220° C.

EXAMPLE 58

Production of 1-[(2-hydroxyethoxy)methyl]-2-thio-6-phenylthiouracil (Compound No. 58)

(1) An amount of 3.84 g (30 mmol) of 2-thiouracil was suspended in 75 ml of methylene chloride, was added to 17.8 ml (72 mmol) of bis(trimethylsilyl)acetamide and 7.2 g (45 mmol) of (2-acetoxyethoxy)methyl acetate and allowed to react at room temperature for 20 minutes. Then, the reaction solution was cooled to 0° C. and added to 4.5 ml (45 mmol) of stannic chloride. After the temperature of the solution had risen to room temperature, the solution was left to react overnight and then added to ice and sodium bicarbonate. After filtering off the deposited solid, the reaction solution was distributed between methylene chloride and aqueous layers. The methylene chloride layer was concentrated to dryness, and the residue was dissolved in a small amount of chloroform, adsorbed on a silica gel column and eluted with 2.5% methanol/chloroform. The eluate was concentrated, and the residue so obtained was dissolved in 5 ml of ethanol, was added to 5 ml of 1N sodium hydroxide aqueous solution and allowed to react at room temperature for 10 minutes. After the reaction, it was neutralized with H+ type cation-exchange resin (Dowex-50). Then, after the removal of the resin by filtration, the reaction solution is concentrated to dryness. The residue was dissolved in 15 ml of dimethylformamide, to this solution 600 mg (4 mmol) of t-butyldimethylsilyl chloride and 270 mg (4 mmol) of imidazole was added and the reaction mixture was allowed to react at room temperature for one hour. Then, the reaction solution was added to 50 ml of water, and the deposited solid was recovered by filtration and dried. The resultant product was recrystallized from toluene/hexane to obtain 716 mg of 1-[(2-t-butyldimethylsilyloxyethoxy)methyl]-2-thiouracil (Yield: 7.5%).
Melting point: 121° C.

(2) Production 1-[(2-t-butyldimethylsilyloxyethoxy)methyl]-2-thio-6-phenylthiouracil (a compound of the general formula VI wherein $R^1$=H, W=TBDMS—O—CH$_2$CH$_2$O-CH$_2$—,

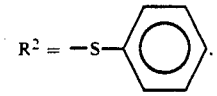

A=—NH—, X=S and Y=O)

In place of 1-[(2-t-butyldimethylsilyloxyethoxy)methyl]thimine in Example 1 (1), 1-[(2-t-butyldimethylsilyloxyethoxy)methyl]-2-thiouracil obtained in the process (1) above was reacted and treated in the same way as in Example 1 to obtain 1-[(2-t-butyl-dimethyl-silyloxyethoxy)methyl]-2-thio-6-phenylthiouracil.
Melting point: 105° C.

(3) In place of 1-[(2-t-butyldimethylsilyloxyethoxy)methyl]-6-phenylthiothymine in Example 1 (2), 123 mg of 1-[(2-t-butyldimethylsilyloxyethoxy)methyl]-2-thio-6-phenylthiouracil produced in the process (2) of this Example was reacted and treated in the same way as in Example 1 (2). The residue was crystallized from water/ethanol to obtain the target compound (Compound No. 58).
Melting point: 146° C.

EXAMPLE 59

Production of 1-[(2-hydroxyethoxy)methyl]-2-thio-6-phenylthiothymine (Compound No. 59)

To 2 ml of tetrahydrofuran, 0.09 ml (0.52 mmol) of 2,2,6,6-tetramethylpiperidine was added. It was then cooled to −70° C., and n-butyl lithium (0.52 mmol) was added thereto in the presence of an argon flow to obtain lithium 2,2,6,6-tetramethylpiperidide solution. Separately, 100 mg (0.24 mmol) of 1-[(2-t-butyldimethylsilyloxyethoxy)methyl]-2-thio-6-phenyluracil was dissolved in 2 ml tetrahydrofuran, and the resulting solution was added dropwise to the above lithium 2,2,6,6-tetramethylpiperidide solution and allowed to react at −70° C. for 1 hour. To this reaction solution, 0.07 ml (1.2 mmol) of methyl iodide was added and allowed to react for 1 hour. Then, after subjected to the same treatment as in Example 1 (1), the resultant was reacted and treated in the same manner as in Example 1 (2). The residue was crystallized from toluene to obtain 39 mg of the target compound (Yield: 60%).

Melting point: 107° C.

EXAMPLE 60

Production of 1-[(2-hydroxyethoxy)methyl]-4-thio-6-phenylthiouracil (Compound No. 60)

An amount of 294 mg (1 mmol) of 1-[(2-hydroxyethoxy)methyl]-6-phenylthiouracil was dissolved in 5 ml pyridine. To this solution 0.17 ml (1.5 mmol) of benzoyl chloride was added and the reaction mixture was allowed to react at room temperature for 2 hours. After the reaction, it was distributed between ethyl acetate and aqueous layers, and the said ethyl acetate layer then concentrated to dryness. The residue was crystallized from toluene to obtain 340 mg of 1-[(2-benzoyloxyethoxy)methyl]-6-phenylthiouracil (Yield: 85%). This was then suspended in 5 ml of toluene, and to this solution 449 mg (1.11 mmol) of 2,4-bis(4-methoxyphenyl)-1,3-dithia-2,4 diphosphetane-2,4-disulfide was added and the reaction mixture was allowed to react at 100° C. for 3 hours. After the reaction, the reaction mixture was distributed between ethyl acetate and aqueous layers, the ethyl actate layer concentrated to dryness. The residue was dissolved in 2 ml of tetrahydrofuran and 5 ml of ethanol. To this solution 2.25 ml of 1N sodium hydroxide aqueous solution was added and the reaction mixture was allowed to react at room temperature for 1 hour. It was then neutralized with hydrochloric acid, and concentrated to dryness. The residue was distributed between ethyl acetate and aqueous layers, and the said ethyl acetate layer was then concentrated to dryness. The resultant was dissolved in a small amount of chloroform, adsorbed on a silica gel column and eluted with 2.5% methanol/chloroform. The eluate was concentrated and dried to obtain a residue, which was crystallized from toluene to obtain 141 mg of the target compound (Yield: 53%).

Melting point: 156° C.

EXAMPLE 61

Production of 1-[(2-hydroxyethoxy)methyl]-4-thio-6-thiothymine (Compound No. 61)

In place of 1-[(2-t-butyldimethylsilyloxyethoxy)methyl]-6-phenylthiouracil in Example 56, 1-[(2-t-butyldimethyloxyethoxy)methyl]-6-phenylthiothymine was reacted and treated in the same manner as in Example 56 except that the crystallization was carried out from toluene to obtain the target compound.

Melting point: 114° C.

Compounds No. 21 and No. 62 to No. 202 may be also produced by analogous methods described above.

EXAMPLE 62

| Production of tablet | |
|---|---|
| 1-[(2-hydroxyethoxy)methyl]-6-phenylthiothymine | 10 g |
| Corn starch | 65 g |
| Carboxycellulose | 20 g |
| Polyvinyl pyrrolidone | 3 g |
| Calcium stearate | 2 g |
| Total amount | 100 g |

The above-mentioned components were well mixed and tablets were produced by a direct tableting method. Each tablet had a weight of 100 mg and contained 10 mg of 1-[(2-hydroxyethoxy)methyl]-6-phenylthiothymine.

EXAMPLE 63

| Production of powder and encapsulated medicine | |
|---|---|
| 1-[(2-hydroxyethoxy)methyl]-6-phenylthiothymine | 20 g |
| Crystalline cellulose | 80 g |
| Total amount | 100 g |

Both components were well mixed to obtain a powder. 100 mg of the thus-obtained powder was charged into a hard capsule of No. 5 to obtain an encapsulated medicine.

EXAMPLE 64

Inhibitory activity for HIV infection

In RPMI 1640 DM culture medium containing 20 mM of Hepes buffer solution, 10% fetal bovine serum and 20 g/ml of gentamycin, $3 \times 10^4$ MT-4 cells (human T cell clone which is destroyed by the infection of HIV) were infected with HIV in an amount of 100 times as large as expected to cause 50% infection of the cells. Immediately thereafter, a predetermined amount of sample was added to the culture medium using 50 mg/ml sample solutions in dimethyl sulfoxide and the cells were cultured at 37° C.

After 5 days of incubation, the number of existing cells was counted to determine the concentration of the compound for preventing the death of 50% of the MT-4 cells. Separately, MT-4 cells were cultured in the same way as above except that they were not infected with HIV to determine the concentration of the compound at which 50% of the MT-4 cells were destroyed.

Both results are shown in Table 2.

TABLE 2

| Compound No. | 50% inhibitory concentration of HIV infection (μM) | 50% cytotoxic concentration to MT-4 cells (μM) |
|---|---|---|
| 1 | 7.0 | >250 |
| 7 | 5.1 | >250 |
| 10 | 13.0 | >250 |
| 12 | 19.0 | >250 |
| 13 | 22.0 | >250 |
| 17 | 34.0 | >250 |
| 25 | 18.0 | >250 |
| 59 | 0.98 | 125 |

EXAMPLE 65

Inhibitory activity for HIV proliferation

In the same culture as that for the MT-4 cells, HUT-78 cells (human T cell clone which is not destroyed by the infection of HIV and releases HIV) were infected with HIV in an amount of 0.4 HIV per HUT-78 cell. Immediately thereafter, a predetermined concentration of 1-[(2-hydroxyethoxy)methyl]-6-phenylthiothymine was added to the culture medium and the cells were cultured at 37° C.

Every four days, 3/4 of the culture solution was exchanged and after 12 days of incubation the number of the cells positive to an HIV antigen was counted by indirect immunofluorescence assay using HIV antiserum (positive to the coating protein and core protein of HIV) which had been obtained from an HIV-infected patient. As a result, the present compound completely prevented the expression of the antigens at the concentration of 20 μM, and 50% inhibitory concentration thereof was proved to be 5.2 μM. When the concentration of the compound was 100 μM, no toxicity to the HUT-78 cells was observed.

For comparison, a similar experiment was carried out by using 2',3'-dideoxyadenosine. This compound completely prevented the expression of the antigen at a similar concentration to the present compound, but it exhibited a significant toxicity to the HUT-78 cells at the concentration of 100 μM.

We claim:

1. A 6-substituted acyclopyrimidine nucleoside compound represented by the formula I:

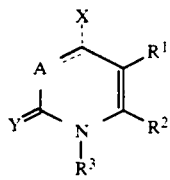

wherein $R^1$ represents a hydrogen or halogen atom or a group of $C_1$ to $C_{10}$ alkyl, $C_2$ to $C_5$ alkenyl, $C_2$ to $C_5$ alkynyl, $C_2$ to $C_5$ alkylcarbonyl, arylcarbonyl, $C_8$ to $C_{12}$ arylcarbonylalkyl, arylthio or $C_7$ to $C_{12}$ aralkyl, the aryl groups thereof optionally being substituted by one or more substituents selected from a halogen atom, $C_1$ to $C_5$ alkyl, $C_1$ to $C_5$ alkoxy, $C_2$ to $C_6$ alkoxycarbonyl, phenyl, naphthyl, carbamoyl, amino, nitro and cyano;

$R^2$ represents a group of arylthio, $C_1$ to $C_5$ alkylthio, $C_3$ to $C_{10}$ cycloalkylthio, aryl sulfoxide, alkyl sulfoxide, $C_3$ to $C_{10}$ cycloalkyl sulfoxide, alkenyl, alkynyl, aralkyl, arylcarbonyl, arylcarbonylalkyl or aryloxy, the aryl groups thereof optionally being substituted by one or more substituents selected from a halogen atom, $C_1$ to $C_5$ alkyl, $C_1$ to $C_5$ alkoxy, $C_2$ to $C_6$ alkylcarbonyl, halogenated methyl, amino, nitro, cyano and hydroxyl;

$R^3$ represents a hydroxyalkyl group of which the alkyl portion contains 2 to 6 carbon atoms and may contain an oxygen atom;

X represents an oxygen or sulfur atom or amino group;

Y represents an oxygen or sulfur atom; and

A represents =N— or —NH—, or a pharmaceutically acceptable salt thereof.

2. A compound according to claim 1, wherein:

$R^1$ represents a hydrogen atom; halogen atom; $C_1$ to $C_{10}$ alkyl group; or a group of $C_2$ to $C_5$ alkenyl, $C_2$ to $C_5$ alkynyl, $C_2$ to $C_5$ alkylcarbonyl, $C_7$ to $C_{11}$ arylcarbonyl, $C_8$ to $C_{12}$ arylcarbonylalkyl, $C_6$ to $C_{10}$ arylthio or $C_7$ to $C_{12}$ aralkyl, the aryl groups thereof optionally being substituted by one or more substituents selected from a halogen atom, $C_1$ to $C_5$ alkyl, $C_1$ to $C_5$ alkoxy, $C_2$ to $C_6$ alkoxycarbonyl, phenyl, naphthyl, carbamoyl, amino, nitro and cyano;

$R^2$ represents a group of $C_6$ to $C_{10}$ arylthio, $C_1$ to $C_5$ alkylthio, $C_3$ to $C_{10}$ cycloalkylthio, $C_6$ to $C_{10}$ aryl sulfoxide, $C_1$ to $C_5$ alkylsulfoxide, $C_3$ to $C_{10}$ cycloalkylsulfoxide, $C_2$ to $C_5$ alkenyl, $C_2$ to $C_5$ alkynyl, $C_7$ to $C_{12}$ aralkyl, $C_7$ to $C_{11}$ arylcarbonyl or $C_6$ to $C_{10}$ aryloxy, the aryl groups thereof optionally being substituted by one or more substituents selected from a halogen atom, $C_1$ to $C_5$ alkyl, $C_1$ to $C_5$ alkoxy, $C_2$ to $C_6$ alkylcarbonyl, halogenated methyl, amino, nitro, cyano and hydroxyl;

$R^3$ represents a hydroxyalkyl group of which alkyl portion contains 2 to 6 carbon atoms and may contain an oxygen atom;

X represents an oxygen or sulfur atom or amino group;

Y represents an oxygen or sulfur atom; and

A represents =N— or —NH—.

3. A compound according to claim 1, wherein:

$R^1$ represents a hydrogen atom; halogen atom; $C_1$ to $C_5$ alkyl; $C_2$ to $C_5$ alkenyl optionally substituted by one or more substituents selected from a halogen atom, $C_1$ to $C_5$ alkoxy, $C_2$ to $C_4$ alkoxycarbonyl, phenyl, naphthyl, carbamoyl, amino, nitro and cyano; $C_2$ to $C_5$ alkynyl optionally substituted by one or more substituents selected from a halogen atom, $C_1$ to $C_5$ alkoxy, phenyl, naphthyl, carbamoyl and amino; $C_2$ to $C_5$ alkylcarbonyl; $C_7$ to $C_{11}$ arylcarbonyl optionally substituted by one or more substituents selected from a halogen atom, $C_1$ to $C_5$ alkyl, $C_1$ to $C_5$ alkoxy, amino, nitro and cyano; $C_8$ to $C_{12}$ arylcarbonylalkyl optionally substituted by one or more substituents selected from a halogen atom, $C_1$ to $C_5$ alkyl, $C_1$ to $C_5$ alkoxy and amino; $C_6$ to $C_{10}$ arylthio group optionally substituted by one or more substituents selected from a halogen atom, $C_1$ to $C_5$ alkyl and $C_1$ to $C_5$ alkoxy; or $C_7$ to $C_{12}$ aralkyl optionally substituted by one or more substituents selected from a halogen atom, $C_1$ to $C_5$ alkyl and $C_1$ to $C_5$ alkoxy;

$R^2$ represents a $C_6$ to $C_{10}$ arylthio optionally substituted by one or more substituents selected from a halogen atom, $C_1$ to $C_5$ alkyl, $C_1$ to $C_5$ alkoxy, $C_2$ to $C_5$ alkylcarbonyl, trifluoromethyl, amino, nitro, cyano and hydroxyl; $C_1$ to $C_5$ alkylthio; $C_3$ to $C_{10}$ cycloalkylthio optionally substituted by one or more substituents selected from a halogen atom, $C_1$ to $C_5$ alkyl, $C_1$ to $C_5$ alkoxy, $C_2$ to $C_5$ alkylcarbonyl, trifluoromethyl and amino; $C_6$ to $C_{10}$ aryl sulfoxide optionally substituted by one or more substituents selected from a halogen atom, $C_1$ to $C_5$ alkyl, $C_1$ to $C_5$ alkoxy, $C_2$ to $C_5$ alkylcarbonyl and amino; $C_1$ to $C_5$ alkyl sulfoxide; $C_3$ to $C_{10}$ cycloalkyl sulfoxide group optionally substituted by one or more substituents selected from a halogen atom, $C_1$ to $C_5$ alkyl, $C_1$ to $C_5$ alkoxy, $C_2$ to $C_5$ alkylcarbonyl and amino; C₂ to C₅ alkenyl optionally substituted by one or more substitutents selected from a halogen atom, C₁ to C₅ alkoxy, C₂ to C₅ alkylcarbonyl, phenyl, naphthyl and amino; C₂ to C₅ alkynyl optionally substituted by one or more substituents selected from a halogen atom, C₁ to C₅ alkoxy, C₂ to C₅ alkylcarbonyl, phenyl, naphthyl and amino; C₇ to C₁₂ aralkyl optionally substituted by one or more substituents selected from a halogen atom, C₁ to C₅ alkyl, C₁ to C₅ alkoxy and C₂ to C₅ alkylcarbonyl; C₇ to C₁₁ arylcarbonyl optionally substituted by one or more substituents selected from a halogen atom, C₁ to C₅ alkyl, C₁ to C₅ alkoxy and C₂ to C₅ alkylcarbonyl; or C₆ to C₁₀ aryloxy optionally substituted by one or more substituents selected from a halogen atom, C₁ to C₅ alkyl, C₁ to C₅ alkoxy, C₂ to C₅ alkylcarbonyl, trifluoromethyl and nitro;

R³ represents a hydroxyalkoxyalkyl group containing 2 to 6 carbon atoms;

X represents an oxygen or sulfur atom or amino group;

Y represents an oxygen or sulfur atom; and

A represents =N— or —NH—.

4. A compound according to claim 3, wherein:

R¹ represents a hydrogen atom; halogen atom; C₁ to C₅ *alkyl*; C₂ to C₅ alkenyl group optionally substituted by one or more substituents selected from a halogen atom, C₂ to C₄ alkoxycarbonyl, phenyl, carbamoyl and cyano; C₂ to C₅ alkynyl optionally substituted by one or more phenyl groups; C₂ to C₅ alkylcarbonyl; C₇ to C₁₁ arylcarbonyl; C₈ to C₁₀ phenylcarbonylalkyl; C₆ to C₁₀ arylthio optionally substituted by one or more C₁ to C₅ alkyl groups; or C₇ to C₉ aralkyl group, R² represents a C₆ to C₁₀ arylthio optionally substituted by one or more substituents selected from a halogen atom, C₁ to C₅ alkyl, C₁ to C₅ alkoxy, C₂ to C₅ alkylcarbonyl, trifluoromethyl, amino, nitro, cyano and hydroxyl; C₁ to C₅ alkylthio; C₃ to C₁₀ cycloalkylthio optionally substituted by one or more substituents selected from a halogen atom, C₁ to C₃ alkyl, C₁ to C₃ alkoxy, C₂ to C₅ alkylcarbonyl and trifluoromethyl; C₆ to C₁₀ aryl sulfoxide; C₁ to C₅ alkyl sulfoxide; C₃ to C₁₀ cycloalkyl sulfoxide; C₂ to C₅ alkenyl optionally substituted by one or more phenyl groups; C₂ to C₅ alkynyl optionally substituted by one or more phenyl groups; C₇ to C₁₁ aralkyl; C₇ to C₁₁ arylcarbonyl; or C₆ to C₁₀ aryloxy optionally substituted by one or more substituents selected from a halogen atom, C₁ to C₅ alkyl, C₁ to C₅ alkoxy, C₂ to C₅ alkylcarbonyl, trifluoromethyl and nitro;

R³ represents a hydroxyalkoxyalkyl group containing 2 to 6 carbon atoms;

X represents an oxygen or sulfur atom or amino group;

Y represents an oxygen or sulfur atom; and

A represents =N— or —NH—.

5. A compound according to claim 4, wherein:

R¹ represents a hydrogen atom; halogen atom; C₁ to C₅ alkyl; or C₂ to C₅ alkenyl;

R² represents a C₆ to C₁₀ arylthio, C₃ to C₁₀ cycloalkylthio or C₇ to C₁₁ aralkyl, those groups optionally substituted by one or more substituents selected from a halogen atom, C₁ to C₅ alkyl, C₁ to C₅ alkoxy and nitro;

R³ represents a hydroxyalkoxyalkyl group containing 2 to 6 carbon atoms;

each of X and Y represents oxygen or sulfur atom; and

A represents =N— or —NH—.

6. A compound according to claim 5, wherein R¹ represents a C₁ to C₃ alkyl group; R² represents a phenylthio group substituted by one or more substituents selected from a chlorine atom, C₁ to C₃ alkyl and C₁ to C₃ alkoxy; R³ represents an ω-hydroxyalkoxyalkyl group containing 2 to 5 carbon atoms; each of X and Y represents oxygen or sulfur atom; and A represents —NH—.

7. A compound according to claim 6, wherein R¹ represents a methyl; R² represents a phenylthio group substituted by one or more substituents selected from a chlorine atom, methyl and methoxy; R³ represents a (2-hydroxyethoxy)methyl group; each of X and Y represents oxygen or sulfur atom; and A represents NH—.

8. A compound according to claim 7, which is 1-[(2-hydroxyethoxy)methyl]-6-phenylthiothymine.

9. A compound according to claim 7, which is 1-[(2-hydroxyethoxy)methyl]-6-(3-methylphenyl-1-thio)thymine.

10. A compound according to claim 7, which is 1-[(2-hydroxyethoxy)methyl]-6-(3-chlorophenyl-1-thio)thymine.

11. A compound according to claim 7, which is 1-[(2-hydroxyethoxy)methyl]-6-(2-methoxyphenyl-1-thio)thymine.

12. A compound according to claim 7, which is 1-[(2-hydroxyethoxy)methyl]-6-(3-methoxyphenyl-1-thio)thymine.

13. A compound according to claim 7, which is 1-[(2-hydroxyethoxy)methyl]-6-(3-nitrophenyl-1-thio)thymine.

14. A compound according to claim 7, which is 1-[(2-hydroxyethoxy)methyl]-6-cyclohexylthiothymine.

15. A compound according to claim 7, which is 1-[(2-hydroxyethoxy)methyl]-2-thio-6-phenylthiothymine.

16. A process for the preparation of a 6-substituted acyclopyrimidine nucleoside compound according to claim 1, which comprises reacting an acyclopyrimidine nucleoside compound represented by the formula II:

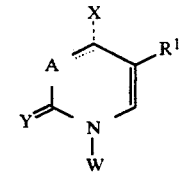

II wherein W represents the group of R³ of which hydroxyl group(s) is (are) protected and R¹R³X, Y and A have the meanings recited in claim 1, with an organic alkali metal compound and a compound of the formula R²X¹ (III) wherein X¹ represents a halogen atom or a group of arylthio or alkoxy and R² have the meaning recited in claim 1, and then eliminating the protective group(s) by deprotection reaction to produce the 6-substituted acyclopyrimidine nucleoside compound.

17. A process for the preparatin of a 6-substituted acyclopyrimidine nucleoside compound according to claim 1, which comprises reacting an acyclopyrimidine nucleoside compound represented by the formula IV:

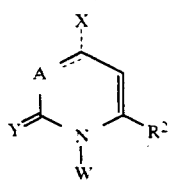

IV wherein W represents the group of R³ of which hydroxyl group(s) is (are) protected and R², R³, X, Y and A have the meanings recited in claim 1, with an organic alkali metal compound and a compound of the formula R¹X² (V) wherein X² represents a halogen atom or a group of arylthio or alkoxy and R¹ have the meaning recited in claim 1, and then eliminating the protective group(s) by deprotection reaction to produce the 6-substituted acyclopyrimidine nucleoside compound.

18. An antiviral composition containing, as an active ingredient, a pharmaceutically effective amount of a 6-substituted acyclopyrimidine nucleoside compound represented by the formula I:

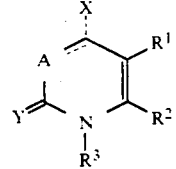

I wherein
R¹ represents a hydrogen or halogen atom or a group of $C_1$ to $C_{10}$ alkyl, $C_2$ to $C_5$ alkenyl, $C_2$ to $C_5$ alkynyl, $C_2$ to $C_5$ alkylcarbonyl, arylcarbonyl, $C_8$ to $C_{12}$ arylcarbonylalkyl, arylthio or $C_7$ to $C_{12}$ aralkyl, the aryl groups thereof optionally being substituted by one or more substituents selected from a halogen atom, $C_1$ to $C_5$ alkyl, $C_1$ to $C_5$ alkoxy, $C_2$ to $C_6$ alkoxycarbonyl, phenyl, naphthyl, carbamoyl, amino, nitro and cyano;

R² represents a group of arylthio, $C_1$ to $C_5$ alkylthio, $C_3$ to $C_{10}$ cycloalkylthio, aryl sulfoxide, alkyl sulfoxide, $C_3$ to $C_{10}$ cycloalkyl sulfoxide, alkenyl, alkynyl, aralkyl, arylcarbonyl, arylcarbonylalkyl or aryloxy, the aryl groups thereof optionally being substituted by one or more substituents selected from a halogen atom, $C_1$ to $C_5$ alkyl, $C_1$ to $C_5$ alkoxy, $C_2$ to $C_6$ alkylcarbonyl, halogenated methyl, amino, nitro, cyano and hydroxyl;

R³ represents a hydroxyalkyl group of which the alkyl portion contains 2 to 6 carbon atoms and may contain an oxygen atom;

X represents an oxygen or sulfur atom or amino group;

Y represents an oxygen or sulfur atom; and

A represents =N— or —NH—, or a pharmaceutically acceptable salt thereof.

* * * * *